(12) United States Patent
Lim et al.

(10) Patent No.: US 7,507,262 B2
(45) Date of Patent: Mar. 24, 2009

(54) COMPOSITIONS FOR OXIDATIVELY DYEING KERATIN FIBERS AND METHODS FOR USING SUCH COMPOSITIONS

(75) Inventors: Mu'lll Lim, West Chester, OH (US); Guiru Zhang, Fairfield, OH (US); Margaret Popp, West Chester, OH (US); Bryan Patrick Murphy, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 75 days.

(21) Appl. No.: 11/715,178

(22) Filed: Mar. 7, 2007

(65) Prior Publication Data

US 2007/0209123 A1    Sep. 13, 2007

Related U.S. Application Data

(60) Provisional application No. 60/779,779, filed on Mar. 7, 2006.

(51) Int. Cl.
*A61Q 5/10*    (2006.01)

(52) U.S. Cl. ................ 8/405; 8/406; 8/435; 8/568; 8/570; 8/573; 8/576; 8/630

(58) Field of Classification Search .............. 8/405, 8/406, 435, 630, 568, 570, 573, 576
See application file for complete search history.

(56) References Cited

U.S. PATENT DOCUMENTS

2004/0147515 A1    7/2004    Umbricht et al.

FOREIGN PATENT DOCUMENTS

| JP | 09197632 A | | 7/1997 |
|---|---|---|---|
| JP | 11147812 | * | 2/1999 |
| JP | 11147812 A | | 6/1999 |
| WO | WO-99/64428 A1 | | 12/1999 |

OTHER PUBLICATIONS

STIC Search Report dated Jul. 10, 2008.*

Bean, et al., "Derivatives of Phenylboric Acid, Their Preparation and Action Upon Bacteria," J. Am. Chem. Soc., vol. 54, p. 4415, (1932).
Ishiyama, T.; Murata, M; Miyaura, N.J. Org. Chem. 1995, 60, 7508.
International Search Report, PCT Application No. PCT/IB2007/050747, dated Dec. 21, 2007 (18 pages).
International Cosmetic Ingredient Dictionary and Handbook, Eighth Edition, The Cosmetic, Toiletry, and Fragrance Association, vol. 2, Section 3, Chemical Classes, and Section 4, Functions (2000).
Chang, Michelle C.Y., et al., "A Selective, Cell-Permeable Optical probe for Hydrogen Peroxide in Living Cells", *JACS Communications, J. Am. Chem. Soc.,* Sep. 24, 2004, p. 15392-15393, vol. 126, Dept. of Chemistry and Molecular and Cell Biology, University of California, Berkeley, CA 94720.
Kuivila, Henry G. and Armour, Albert G., "Electrophilic Displacement Reactions. IX. Effects of Substituents on Rates of Reactions between Hydrogen Peroxide and Benzeneboronic Acid", *Organic and Biological Chemistry*, Apr. 8, 1957, p. 5659-5662, vol. 79, Department of Chemistry, University of New Hampshire.
Miller, Evean W. et al., "Boronate-Based Fluorescent Probes for Imaging Cellular Hyrdrogen Peroxide", *JACS Articles, J. Am. Chem. Soc.,* Jul. 6, 2005, p. 16652-16659, vol. 127, Dept. of Chemistry and Molecular and Cell Biology, University of California, Berkeley, CA 94720.
Webb, Kevin S. and Levy, Daniel, "A Facile Oxidation of Boronic Acids and Boronic Esters", *Pergamon, Tetrahedron Letters*, May 26, 1995, p. 5117-5118, vol. 36, No. 29, Elsevier Science Ltd., Great Britain.

\* cited by examiner

*Primary Examiner*—Eisa B Elhilo
(74) *Attorney, Agent, or Firm*—Melissa Krasovec; Marianne Dressman; Tara Rosnell

(57) ABSTRACT

Compositions for dyeing keratin fibers comprise (a) at least one keratin dyeing compound selected from aromatic systems which comprise at least one boronic acid or boronic ester moiety and which are capable of forming upon oxidation a nucleophile or an electrophile, (b) at least one additional keratin dyeing compound selected from the group consisting of auxiliary developers and auxiliary couplers, and (c) a cosmetically suitable medium. Methods for oxidatively dyeing keratin fibers comprise the steps of applying such compositions in the presence of an oxidizing agent and rinsing the hair. A hair coloring product in kit form comprises a first separately packaged container comprising a composition as described above and a second separately packaged container comprising an oxidizing agent.

22 Claims, No Drawings

COMPOSITIONS FOR OXIDATIVELY DYEING KERATIN FIBERS AND METHODS FOR USING SUCH COMPOSITIONS

CROSS REFERENCE TO RELATED APPLICATIONS

This application claims the benefit of U.S. Provisional application Ser. No. 60/779,779 filed on Mar. 7, 2006.

FIELD OF THE INVENTION

The present invention relates to compositions for oxidatively dyeing keratin fibers and methods for using such compositions. More particularly, the present invention relates to such compositions comprising aromatic systems which comprise at least one boronic acid or boronic ester moiety and which are capable of forming upon oxidation a nucleophile or an electrophile.

BACKGROUND OF THE INVENTION

The most extensively used method currently employed to dye keratin fibers, such as hair, is by an oxidative process that utilizes one or more oxidative dye compounds in combination with one or more oxidizing agents.

Commonly, a peroxy oxidizing agent is used in combination with one or more developers or couplers, which are generally small molecules capable of diffusing into hair. A wide variety of oxidants may be used to generate the reactive developer species. Generally, a peroxide material, such as hydrogen peroxide, activates the developers so that they react with the couplers to form larger sized compounds in the hair shaft to give a variety of shades and colors.

A wide variety of developers and couplers have been employed in such oxidative hair coloring systems and compositions. However, there still exists a need for additional keratin dyeing compounds which can act as developers and/or couplers and which can safely provide color benefits.

Hydrogen peroxide-mediated transformation of arylboronic acids or arylboronic esters to phenols has been investigated to develop highly selective and sensitive probes for hydrogen peroxide, which is one of the major reactive oxygen species ("ROS") in living cells. The kinetics of the reaction between hydrogen peroxide and phenylboronic acid was investigated by Henry G. Kuivila et al., *J. Am. Chem. Soc.* 1957, 79, 5659, who proposed the following mechanism:

Additionally, the transformation of boronic acids and boronic esters to the corresponding alcohols by the use of Oxone™ in aqueous acetone buffered with sodium bicarbonate has been described by Kevin S. Webb et al., Tetrahedron Letters, 1995, 36, 5117.

More recently, the syntheses and biological applications of fluorescent probes for hydrogen peroxide have been reported by Michelle C. Y. Chang et al., *J. Am Chem. Soc.*, 2004, 126, 15392 and 2005, 127, 16652. These peroxysensors utilize a boronate-hydrogen peroxide reaction to provide high selectivity for detecting hydrogen peroxide in aqueous solution. The boronate compound is non-fluorescent and displays no absorption in the visible region. The addition of hydrogen peroxide triggers immediate increase in fluorescence and growth of visible wavelength absorption bands characteristic fluorescein and red-fluorescent resorufin, as shown in the following mechanisms, respectively:

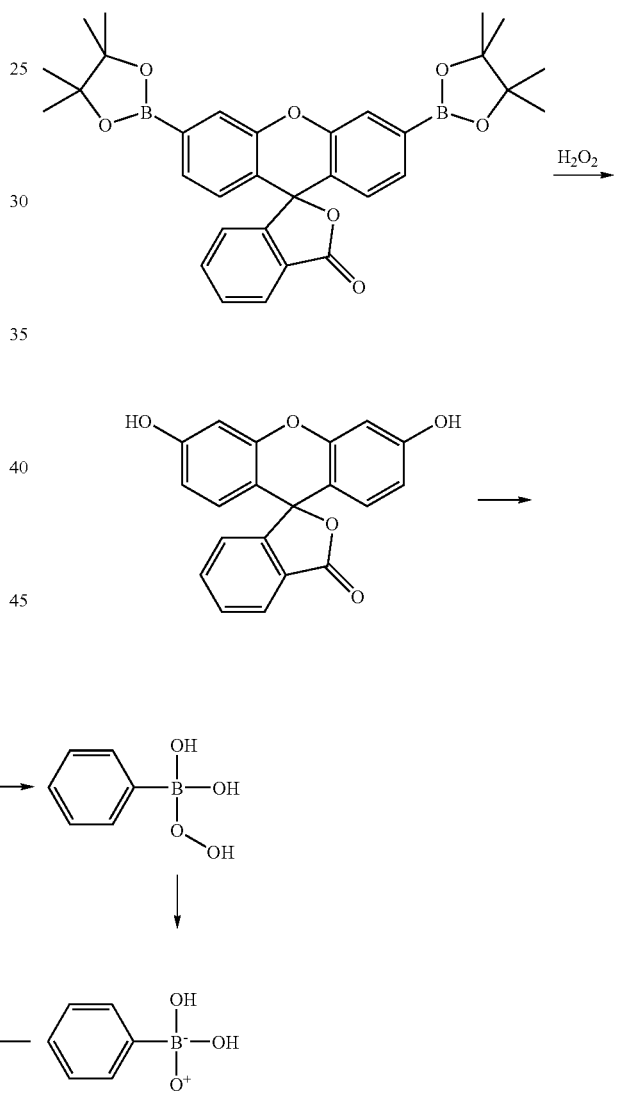

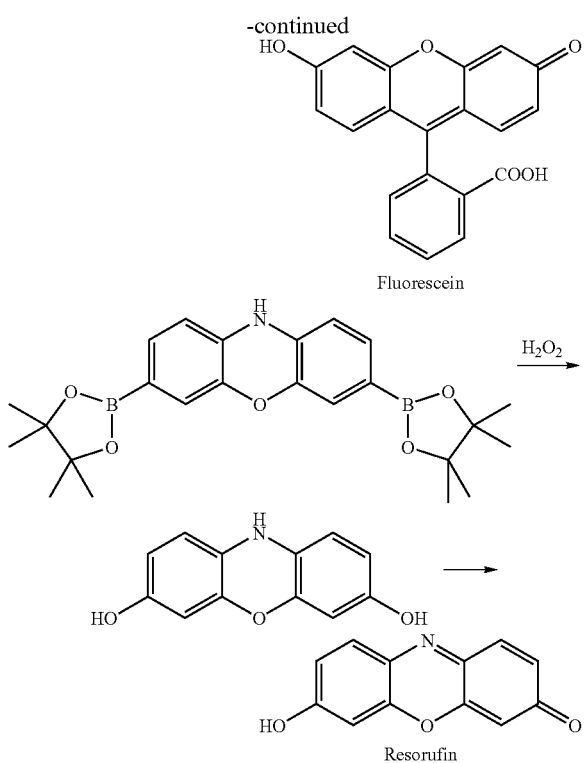

Fluorescein

Resorufin

The aforementioned references, however, do not disclose the use of such boronic acid and boronic ester compounds in compositions for oxidatively dyeing keratin fibers.

It has now been discovered that certain aromatic systems comprising at least one boronic acid or boronic ester moiety are capable of imparting commercially desirable colors to keratin fibers, such as hair. Such boronic acid or boronic ester compounds are capable of providing dyeing results comparable, in terms of color and intensity, to those achieved by using known oxidative dye compounds. Accordingly, there exists a need for keratin fiber dyeing compositions which comprise aromatic systems comprising at least one boronic acid or boronic ester moiety.

SUMMARY OF THE INVENTION

The present invention relates to compositions for dyeing keratin fibers, the compositions comprising (a) at least one keratin dyeing compound selected from aromatic systems which comprise at least one boronic acid or boronic ester moiety and which are capable of forming upon oxidation a nucleophile or an electrophile, (b) at least one additional keratin dyeing compound selected from the group consisting of auxiliary developers and auxiliary couplers, and (c) a cosmetically suitable medium. The keratin dyeing compounds of the present invention, which comprise a boronic acid or boronic ester moiety, may act as a coupler or as a developer or may self-couple to produce a color in keratin fibers.

The present invention further relates to a method for oxidatively dyeing keratin fibers, the method comprising the steps of applying such compositions in the presence of an oxidizing agent and rinsing the hair.

The present invention also further relates to a kit for treating hair, the kit comprising a first separately packaged container comprising a composition of the present invention and a second separately packaged container comprising an oxidizing agent.

DETAILED DESCRIPTION OF THE INVENTION

While the specification concludes with claims that particularly point out and distinctly claim the invention, it is believed the present invention will be better understood from the following description.

As used herein, "comprising" means that other steps and other ingredients which do not affect the end result can be added. This term encompasses the terms "consisting of" and "consisting essentially of". The compounds/compositions and methods/processes of the present invention can comprise, consist of, and consist essentially of the essential elements and limitations of the invention described herein, as well as any of the additional or optional ingredients, components, steps, or limitations described herein.

All percentages, parts and ratios are based upon the total weight of the compositions of the present invention, unless otherwise specified. All such weights as they pertain to listed ingredients are based on the active level, and, therefore, do not include solvents or by-products that may be included in commercially available materials, unless otherwise specified. The term "weight percent" may be denoted as "wt. %" herein.

Except as otherwise noted, all amounts including part, percentages, and proportions are understood to be modified by the word "about", and amounts are not intended to indicate significant digits. Except as otherwise noted, the articles "a", "an", and "the" mean "one or more".

As used herein, the term "keratin" refers to a scleroprotein found in epidermal tissues and modified into hard structures such as horns, hair, and nails. Thus, the term "keratin fibers" or "keratinous fibers" refers to those found in hair, skin and nails, and various animal body parts such as horns, hooves and feathers.

As used herein, the term "hair" refers to keratinous fibers on a living (e.g., a person) or non-living body (e.g., in a wig, hairpiece, or other aggregation of non-living keratinous fibers). Mammalian, preferably human, hair is a preferred. Notably, hair, wool, fur, and other keratinous fibers are suitable substrates for coloring by the compounds and compositions described herein.

As used herein, the term "keratin dyeing compounds" refers to compounds that may be used in the composition to act as developers, couplers, or both, in order to provide color to keratin fibers.

As used herein, the term "keratin dyeing composition" refers to the composition containing one or more keratin dyeing compounds, including the compounds described herein.

As used herein, "cosmetically acceptable" means that ingredients which the term describes are suitable for use in contact with the skin or hair of humans and lower animals without undue toxicity, incompatibility, instability, irritation, allergic response, and the like.

It is understood that within the scope of this invention, numerous potentially and actually tautomeric compounds are involved. As a general example of tautomerism, 2-mercaptopyridine (I) exists under known conditions in the pyridine-2-thione tautomer form (II).

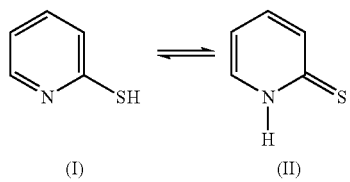

(I)            (II)

It is to be understood that when this description refers to a particular structure, all of the reasonable additional tautomeric structures are included. In the art, tautomeric structures are frequently represented by one single structure and the present invention follows this general practice.

The keratin dyeing compositions of the present invention comprise (a) at least one keratin dyeing compound selected from aromatic systems which comprise at least one boronic acid or boronic ester moiety and which are capable of forming upon oxidation a nucleophile or an electrophile, (b) at least one additional keratin dyeing compound selected from the group consisting of auxiliary developers and auxiliary couplers, and (c) a cosmetically suitable medium. Each of these components, as well as preferred and/or optional additional components, is described in detail hereinafter.

I. Compositions for Oxidatively Dyeing Keratin Fibers

A. Boronic Acid and Boronic Ester Keratin Dyeing Compounds

The compositions for dyeing keratin fibers of the present invention comprise at least one keratin dyeing compound selected from aromatic systems which comprise at least one boronic acid or boronic ester moiety and and which are capable of forming upon oxidation a nucleophile or an electrophile. As used herein, the term "aromatic system" refers to a substituted mono- or poly-cyclic hydrocarbon ring which includes, optionally, one or more heteroatoms in the ring, and which has a cyclic, planar, and conjugated pi-electron system with the number of delocalized pi-electrons being (4n+2) wherein n is an integer. As used herein, the term "nucleophile" refers to a neutral or negatively charged chemical species which is attracted to positive sources such as nuclei and which tends to donate or share electrons in order to form a chemical bond. As used herein, the term "electrophile" refers to a neutral or positively charged chemical species which is attracted to negative sources and which tends to accept electron pairs in order to form a chemical bond.

The aromatic systems of the present invention include, but are not limited to, compounds according to one of the following formulas I to XV:

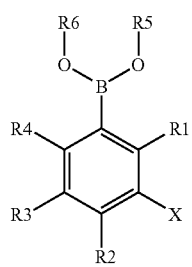

I

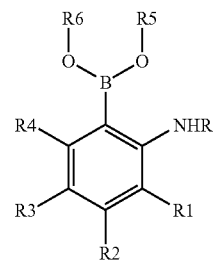

II

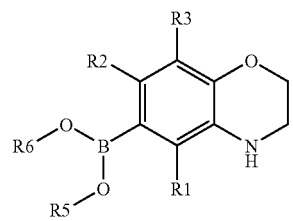

III

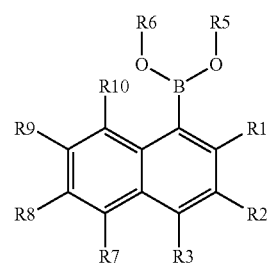

IV

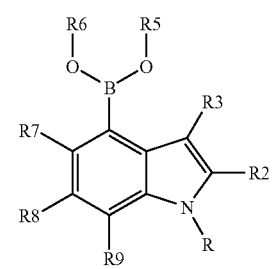

V

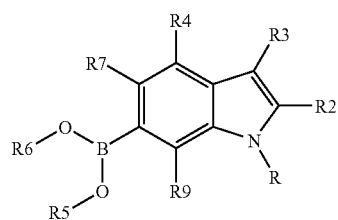

VI

VII

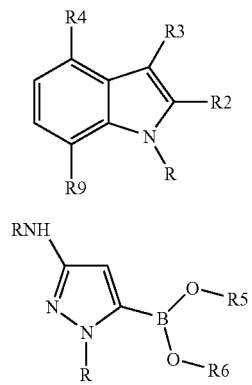

VIII

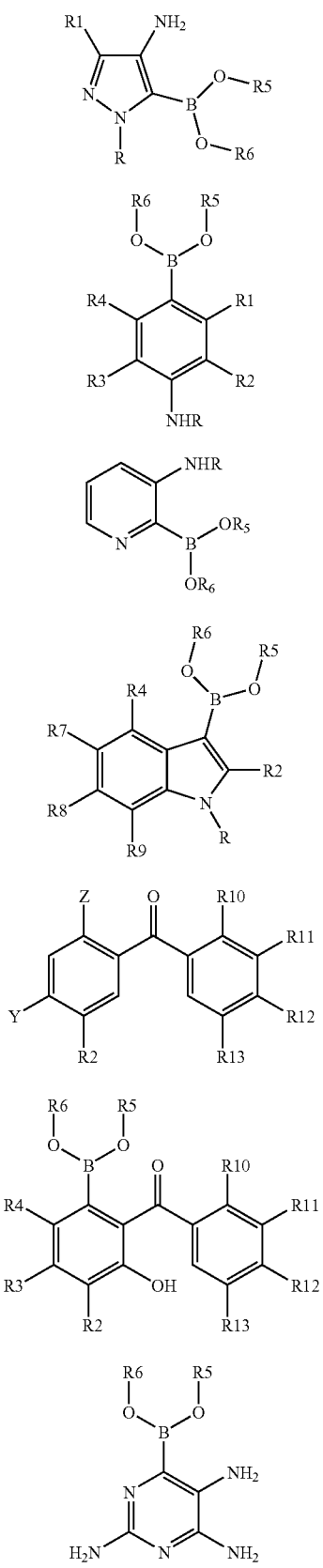

wherein R1, R2, R3, R4, R7, R8, R9, R10, R11, R12, and R13 each are independently selected from the group consisting of:
(a) C-linked monovalent substituents selected from the group consisting of:
  (i) substituted or unsubstituted, straight or branched, alkyl, mono- or poly-unsaturated alkyl, heteroalkyl, aliphatic, heteroaliphatic, or heteroolefinic systems,
  (ii) substituted or unsubstituted, mono- or poly-cyclic aliphatic, aryl, or heterocyclic systems, and
  (iii) substituted or unsubstituted, mono-, poly-hydroxy or -fluoro alkyl systems;
  wherein said systems of (i), (ii) and (iii) comprise from about 1 to about 10 carbon atoms and from about 0 to about 5 heteroatoms selected from the group consisting of O, S, N, P, and Si;
(b) S-linked monovalent substituents selected from the group consisting of $SA^1$,
(c) O-linked monovalent substituents selected from the group consisting of $OA^1$;
(d) N-linked monovalent substituents selected from the group consisting of $NA^1A^2$;
(e) a halogen selected from the group consisting of F, Cl, Br, and I;
(f) fluoroalkyl monovalent substituents selected from the group consisting of mono-, poly-, and per-fluoro alkyl systems comprising from about 1 to about 12 carbon atoms and from about 0 to about 4 heteroatoms; and
(g) hydrogen; and
wherein R is selected group consisting of hydrogen, COR1, and said C-linked monovalent substituents of (a);
wherein R5 and R6 each are independently selected from the group consisting of hydrogen and lower alkyl groups which can be joined together as a straight or branched alkylene chain forming a five or six-membered ring or an aromatic ring;
wherein X is selected from the group consisting of hydroxyl, B(OR5)OR6, and NA1A2;
wherein Y and Z each are independently selected from the group consisting of hydroxyl and B(OR5)OR6, provided that at least one of which is B(OR5)OR6; and
wherein $A^1$ and $A^2$ are monovalent and are independently selected from the group consisting of hydrogen; substituted or unsubstituted, straight or branched, alkyl, mono- or poly-unsaturated alkyl, heteroalkyl, aliphatic, heteroaliphatic, or heteroolefinic systems; substituted or unsubstituted, mono- or poly-cyclic aliphatic, aryl, or heterocyclic systems; and substituted or unsubstituted, mono-, poly-, per-fluoro alkyl systems; or $A^1$ and $A^2$ together with a nitrogen atom to which they are bound form a ring; wherein all of said systems comprise from about 1 to about 10 carbon atoms and from about 0 to about 5 heteroatoms selected from the group consisting of O, S, N, P, and Si.

In one embodiment of the present invention, R1, R2, R3, R4, R7, R8, R9, R10, R11, R12, and R13 each are independently selected from the group consisting of a hydrogen atom; a halogen atom such as chlorine, bromine, iodine or fluorine; an amino radical, a hydroxyl radical; a cyano radical; a $C_1$-$C_4$ alkyl radical; a trifluoromethyl radical, an alkylamino radical (e.g., N,N-dimethylamino, N,N-diethylamino, N-methylamino, or N-ethylamino); a hydroxyalkylamino radical (e.g., N-(hydroxyethyl)amino, N-hydroxymethylamino, N-hydroxypropylamino, N,N-bis(hydroxyethyl)amino, N-(2,3-dihydroxypropyl)amino or N,N-bis(hydroxypropyl)amino); an acetylamido radical; a carboxyl radical; an alkoxy radical (e.g., methoxy, ethoxy, propyloxy, benzyloxy, methoxyethoxy, phenoxyethoxy, 2-cyanoethoxy, phenethyloxy, phenoxyethoxy, p-chlorobenzyloxy or methoxyethylcarbamoylmethoxy); an alkoxyalkyl radical (e.g., methoxymethyl, methoxyethyl, methoxypropyl, ethoxymethyl, ethoxyethyl or ethoxypropyl); a carbamoyl radical; an alkylcarbamoyl radical (e.g., methylcarbamoyl, ethylcarbamoyl, dimethylcarbamoyl, or diethylcarbamoyl); a hydroxyalkylcarbamoyl radical (e.g., 2-hydroxyethylcarbamoyl, bis(2-hydroxyethyl)carbamoyl, hydroxymethylcarbamoyl, bis(hydroxymethyl)carbamoyl); an amido radical; an alkylamido radical (e.g., acetamido, propionamido, or butyramido); an alkylcarbonyl radical (e.g., acetyl, butyryl, or propionyl), an alkoxycarbonyl radical (e.g., methoxycarbonyl, ethoxycarbonyl, or propoxycarbonyl); an aryloxy radical (e.g., phenoxy, 4-methoxyphenoxy, 4-nitrophenoxy, 4-cyanophenoxy, 4-methanesulfonamidophenoxy, 4-methanesulfonylphenoxy, 3-methylphenoxy or 1-naphthyloxy); an acyloxy radical (e.g., acetoxy, propanoyloxy, benzolyloxy, 2,4-dichlorobenzolyloxy, ethoxyalkyloxy, pyruviloyloxy, cinnamoyloxy or myristoyloxy); an alkylthio radical (e.g., methylthio, ethylthio, propylthio, butylthio, 2-cyanoethylthio, benzylthio, phenethylthio, 2-(diethylamino)ethylthio, ethoxyethylthio or phenoxyethylthio); an arylthio radical (e.g., phenylthio, 4-carboxyphenylthio, 2-ethoxy-5-tert-butylphenylthio, 2-carboxyphenylthio or 4-methanesulfonylphenylthio); a heteroarylthio radical (e.g., 5-phenyl-2,3,4,5-tetrazolyloxy or 2-benzothiazolyloxy); a heteroaryloxy radical (e.g., 5-phenyl-2,3,4,5-tetrazolyloxy or 2-benzothiazolyloxy); a 5- or 6-membered heterocycle having at least one nitrogen, oxygen or sulfur atom (e.g., pyridyl, quinolyl, morpholyl, furyl, tetrahydrofuryl, pyrazolyl, triazolyl, tetrazolyl, triazolyl, oxazolyl, imidazolyl or thiadiazolyl) and being optionally substituted; an aryl radical (e.g., phenyl or naphthyl) which is optionally substituted; a sulfonyl radical; a sulfinyl radical; a phosphonyl radical; a sulfamoyl radical; a siloxy radical; an acyloxy radical; a carbamoyloxy radical; a sulphonamide radical; an imide radical; a ureido radical; a sulfamoylamino radical; an alkoxycarbonylamino radical; an aryloxycarbonylamino radical; an aryloxycarbonyl radical; and a benzenesulfonamido radical.

The keratin dyeing compounds of the present invention which are aromatic systems comprising at least one boronic acid or boronic ester moiety may act upon oxidation as a coupler or as a developer or may self-couple to produce a color in keratin fibers.

When utilized as a coupler, the compounds of the present invention may accommodate a nucleofugic leaving group at a potential coupling position. Suitable nucleofugi leaving groups include, but are not limited to, those selected from the group consisting of hydrogen, chlorine, cyano, alkoxy, phenoxy, methylsulfonyoxy, pyridine, and pyridazone.

In an embodiment of the present invention, the boronic acid or boronic ester compounds of the present invention are couplers and are utilized in compositions together with developers that are pyrazoles. In a further embodiment, the couplers of the present invention are utilized in compositions together with one or more of the following pyrazole developers: 1-methyl-1H-pyrazole-4,5-diamine, 2-(4,5-diamino-1H-pyrazol-1-yl)ethanol, 1-isopropyl-1H-pyrazole-4,5-diamine, 1-(4-methylbenzyl)-1H-pyrazole-4,5-diamine, 1-(benzyl)-1H-pyrazole-4,5-diamine, 1-(4-chlorobenzyl)-1H-pyrazole-4,5-diamine and 1-hydroxyethyl-4,5-diaminopyrazole sulfate. In a preferred embodiment, the couplers of the present invention are utilized in compositions together with at least one pyrazole developer compound selected from 1-methyl-1H-pyrazole-4,5-diamine; 1-hydroxyethyl-4,5-diaminopyrazole sulfate; and 2-(4,5-diamino-1H-pyrazol-1-yl)ethanol. While not being bound to theory, it is believed that such combinations enable the desired achievement of more bathochromic colors (e.g., blue) relative to conventional combinations of developers and couplers.

Exemplified Compounds of Formulas I to XV

Non-limiting examples of keratin dyeing compounds selected from aromatic systems comprising at least one boronic acid or boronic ester moiety, which are representative of compounds according to formulas I to XV of the present invention, are provided in the following.

1. Exemplified Compounds of Formula I

Exemplified compounds according to Formula I include, but are not limited to, 3-hydroxyphenylboronic acid, 3-hydroxy-2-methylphenylboronic acid, 2-chloro-5-hydroxyphenylboronic acid, 6-chloro-3-hydroxy-2-methylphenylboronic acid, 3-hydroxy-6-methoxy-2-methylphenylboronic acid, 3-hydroxy-2,4-dimethylphenylboronic acid, 2-ethyl-3-hydroxyphenylboronic acid, 3-hydroxy-2-(2-hydroxyethyl)phenylboronic acid, 2-(2,2,2-trifluoroethyl)-3-hydroxyphenylboronic acid, 2-(cyanomethyl)-3-hydroxyphenylboronic acid, 3-(4,4,5,5-tetramethyl-1,3,2-dioxaborolan-2-yl)phenol, 2-methyl-3-(4,4,5,5-tetramethyl-1,3,2-dioxaborolan-2-yl)phenol, 4-chloro-3-(4,4,5,5-tetramethyl-1,3,2-dioxaborolan-2-yl)phenol, 4-chloro-2-methyl-3-(4,4,5,5-tetramethyl-1,3,2-dioxaborolan-2-yl)phenol, 4-methoxy-2-methyl-3-(4,4,5,5-tetramethyl-1,3,2-dioxaborolan-2-yl)phenol, 2,6-dimethyl-3-(4,4,5,5-tetramethyl-1,3,2-dioxaborolan-2-yl)phenol, 2-ethyl-3-(4,4,5,5-tetramethyl-1,3,2-dioxaborolan-2-yl)phenol, 2-(2-hydroxyethyl)-3-(4,4,5,5-tetramethyl-1,3,2-dioxaborolan-2-yl)phenol, 3-(5,5-dimethyl-1,3,2-dioxaborinan-2-yl)phenol, 2-methyl-3-(5,5-dimethyl-1,3,2-dioxaborinan-2-yl)phenol, 3-(benzo[d][1,3,2]dioxaborol-2-yl)phenol, 3-(benzo[d][1,3,2]dioxaborol-2-yl)-2-methylphenol, 3-(1,3,2-dioxaborolan-2-yl)phenol, 3-(1,3,2-dioxaborolan-2-yl)-2-methylphenol, 3-aminophenylboronic acid, 3-amino-2-methylphenylboronic acid, 3-(methylamino)phenylboronic acid, 3-(2-hydroxyethylamino)phenylboronic acid, 3-[bis(2-hydroxyethyl)amino]phenylboronic acid, 3-morpholinophenylboronic acid, 3-(pyrrolidin-1-yl)phenylboronic acid, 3-amino-4-chlorophenylboronic acid, 5-amino-2,4-dichlorophenylboronic acid, 5-amino-2-methoxyphenylboronic acid, 3-amino-4-methoxyphenylboronic acid, 3-(4,4,5,5-tetramethyl-1,3,2-dioxaborolan-2-yl)benzenamine, 3-(5,5-dimethyl-1,3,2-dioxaborinan-2-yl)benzenamine, 3-(1,3,2-dioxaborolan-2-yl)benzenamine, and 3-(benzo[d][1,3,2]dioxaborol-2-yl)benzenamine.

2. Exemplified Compounds of Formula II

Exemplified compounds according to Formula II include, but are not limited to, 2-aminophenylboronic acid, 2-amino-5-methylphenylboronic acid, 2-amino-5-ethylphenylboronic acid, 2-amino-4-chlorophenylboronic acid, 2-amino-4-methoxyphenylboronic acid, 2-(2-hydroxyethylamino)phenylboronic acid, 2-[bis(2-hydroxyethyl)amino]phenylboronic acid, 2-morpholinophenylboronic acid, 2-(pyrrolidin-1-yl)phenylboronic acid, 2-(methylamino)phenylboronic acid, 2-(4,4,5,5-tetramethyl-1,3,2-dioxaborolan-2-yl)benzenamine, 4-methyl-2-(4,4,5,5-tetramethyl-1,3,2-dioxaborolan-2-yl)benzenamine, 2-(1,3,2-dioxaborolan-2-yl)benzenamine, 2-(benzo[d][1,3,2]dioxaborol-2-yl)benzenamine, and 2-(5,5-dimethyl-1,3,2-dioxaborinan-2-yl)benzenamine.

3. Exemplified Compounds of Formula III

Exemplified compounds according to Formula III include, but are not limited to, 3,4-dihydro-2H-benzo[b][1,4]oxazin-6-yl-6-boronic acid, 3,4-dihydro-7-methyl-2H-benzo[b][1,4]oxazin-6-yl-6-boronic acid, 7-ethyl-3,4-dihydro-2H-benzo[b][1,4]oxazin-6-yl-6-boronic acid, 3,4-dihydro-7-methoxy- 2H-benzo[b][1,4]oxazin-6-yl-6-boronic acid, 6-(1,3,2-dioxaborolan-2-yl)-3,4-dihydro-2H-benzo[b][1,4]oxazine, 6-(benzo[d][1,3,2]dioxaborol-2-yl)-3,4-dihydro-2H-benzo[b][1,4]oxazine, and 3,4-dihydro-6-(5,5-dimethyl-1,3,2-dioxaborinan-2-yl)-2H-benzo[b][1,4]oxazine.

4. Exemplified Compounds of Formula IV

Exemplified compounds according to Formula IV include, but are not limited to, naphthalen-1-yl-1-boronic acid, 2-methylnaphthalen-1-yl-1-boronic acid, 2-ethylnaphthalen-1-yl-1-boronic acid, 4-chloronaphthalen-1-yl-1-boronic acid, 4-methoxynaphthalen-1-yl-1-boronic acid, 4,4,5,5-tetramethyl-2-(naphthalen-4-yl)-1,3,2-dioxaborolane, 4,4,5,5-tetramethyl-2-(2-methylnaphthalen-1-yl)-1,3,2-dioxaborolane, 2-(naphthalen-4-yl)-1,3,2-dioxaborolane, 2-(naphthalen-4-yl)benzo[d][1,3,2]dioxaborole, 5,5-dimethyl-2-(naphthalen-4-yl)-1,3,2-dioxaborinane, 7-methylnaphthalen-1-yl-1-boronic acid, 6-methylnaphthalen-1-yl-1-boronic acid, 8-methylnaphthalen-1-yl-1-boronic acid, 2-(2,2,2-trifluoroethyl)naphthalen-1-yl-1-boronic acid, and 2-(2-hydroxyethyl)naphthalen-1-yl-1-boronic acid.

5. Exemplified Compounds of Formula V

Exemplified compounds according to Formula V include, but are not limited to, 1H-indol-4-yl-4-boronic acid, 7-chloro-1H-indol-4-yl-4-boronic acid, 7-methoxy-1H-indol-4-yl-4-boronic acid, 2-methyl-1H-indol-4-yl-4-boronic acid, 2,3-dimethyl-1H-indol-4-yl-4-boronic acid, 5-methyl-1H-indol-4-yl-4-boronic acid, 1-methyl-1H-indol-4-yl-4-boronic acid, 4-(4,4,5,5-tetramethyl-1,3,2-dioxaborolan-2-yl)-1H-indole, 4-(1,3,2-dioxaborolan-2-yl)-1H-indole, 4-(benzo[d][1,3,2]dioxaborol-2-yl)-1H-indole, and 4-(5,5-dimethyl-1,3,2-dioxaborinan-2-yl)-1H-indole.

6. Exemplified Compounds of Formula VI

Exemplified compounds according to Formula VI include, but are not limited to, 1H-indol-6-yl-6-boronic acid, 2-methyl-1H-indol-6-yl-6-boronic acid, 2,3-dimethyl-1H-indol-6-yl-6-boronic acid, 7-methyl-1H-indol-6-yl-6-boronic acid, 1-methyl-1H-indol-6-yl-6-boronic acid, 5-chloro-1H-indol-6-yl-6-boronic acid, 5-methoxy-1H-indol-6-yl-6-boronic acid, 6-(4,4,5,5-tetramethyl-1,3,2-dioxaborolan-2-yl)-1H-indole, 6-(1,3,2-dioxaborolan-2-yl)-1H-indole, 6-(benzo[d][1,3,2]dioxaborol-2-yl)-1H-indole, and 6-(5,5-dimethyl-1,3,2-dioxaborinan-2-yl)-1H-indole.

7. Exemplified Compounds of Formula VII

Exemplified compounds according to Formula VII include, but are not limited to, 5-hydroxy-1H-indol-6-yl-6-boronic acid, 6-hydroxy-1H-indol-5-yl-5-boronic acid, 5-hydroxy-2-methyl-1H-indol-6-yl-6-boronic acid, 6-hydroxy-2-methyl-1H-indol-5-yl-5-boronic acid, 5-hydroxy-2,3-dimethyl-1H-indol-6-yl-6-boronic acid, 6-hydroxy-2,3-dimethyl-1H-indol-5-yl-5-boronic acid, 5-hydroxy-1-methyl-1H-indol-6-yl-6-boronic acid, 6-hydroxy-1-methyl-1H-indol-5-yl-5-boronic acid, 5-hydroxy-1-(2-hydroxyethyl)-1H-indol-6-yl-6-boronic acid, 6-hydroxy-1-(2-hydroxyethyl)-1H-indol-5-yl-5-boronic acid, 6-(4,4,5,5-tetramethyl-1,3,2-dioxaborolan-2-yl)-1H-indol-5-ol, 5-(4,4,5,5-tetramethyl-1,3,2-dioxaborolan-2-yl)-1H-indol-6-ol, 6-(1,3,2-dioxaborolan-2-yl)-1H-indol-5-ol, 5-(5,5-dimethyl-1,3,2-dioxaborinan-2-yl)-1H-indol-6-ol, 2-methyl-6-(4,4,5,5-tetramethyl-1,3,2-dioxaborolan-2-yl)-1H-indol-5-ol, and 2-methyl-5-(4,4,5,5-tetramethyl-1,3,2-dioxaborolan-2-yl)-1H-indol-6-ol.

8. Exemplified Compounds of Formula VIII

Exemplified compounds according to Formula VII include, but are not limited to, 1-ethyl-3-(methylamino)-1H-pyrazol-5-yl-5-boronic acid, 1-(2-hydroxyethyl)-3-(methylamino)-1H-pyrazol-5-yl-5-boronic acid, 3-acetamido-1-(2-hydroxyethyl)-1H-pyrazol-5-yl-5-boronic acid, 3-(2-hydroxyethylamino)-1-(2-hydroxyethyl)-1H-pyrazol-5-yl-5-boronic acid, 1-methyl-3-(methylamino)-1H-pyrazol-5-yl-5-boronic acid, 5-(1,3,2-dioxaborolan-2-yl)-N,1-dimethyl-1H-pyrazol-3-amine, 2-(3-(ethylamino)-5-(4,4,5,5-tetramethyl-1,3,2-dioxaborolan-2-yl)-1H-pyrazol-1-yl)ethanol, N-(1-(2-hydroxyethyl)-5-(5,5-dimethyl-1,3,2-dioxaborinan-2-yl)-1H-pyrazol-3-yl)acetamide, 3-amino-1-phenyl-1H-pyrazol-5-yl-5-boronic acid, and N-(5-(benzo[d][1,3,2]dioxaborol-2-yl)-1-(2-hydroxyethyl)-1H-pyrazol-3-yl)acetamide.

9. Exemplified Compounds of Formula IX

Exemplified compounds according to Formula IX include, but are not limited to, 4-amino-1-methyl-1H-pyrazol-5-yl-5-boronic acid, 4-amino-1-ethyl-1H-pyrazol-5-yl-5-boronic acid, 4-amino-1-(2-hydroxyethyl)-1H-pyrazol-5-yl-5-boronic acid, 4-amino-1-(2-hydroxyethyl)-3-methyl-1H-pyrazol-5-yl-5-boronic acid, 4-amino-1-benzyl-1H-pyrazol-5-yl-5-boronic acid, 4-amino-1-isopropyl-1H-pyrazol-5-yl-5-boronic acid, 5-(1,3,2-dioxaborolan-2-yl)-1-methyl-1H-pyrazol-4-amine, 5-(1,3,2-dioxaborolan-2-yl)-1-ethyl-1H-pyrazol-4-amine, 2-(4-amino-5-(1,3,2-dioxaborolan-2-yl)-1H-pyrazol-1-yl)ethanol, 2-(4-amino-5-(1,3,2-dioxaborolan-2-yl)-3-methyl-1H-pyrazol-1-yl)ethanol, 1-benzyl-5-(1,3,2-dioxaborolan-2-yl)-1H-pyrazol-4-amine, 5-(1,3,2-dioxaborolan-2-yl)-1-isopropyl-1H-pyrazol-4-amine, 1-methyl-5-(4,4,5,5-tetramethyl-1,3,2-dioxaborolan-2-yl)-1H-pyrazol-4-amine, 1-ethyl-5-(4,4,5,5-tetramethyl-1,3,2-dioxaborolan-2-yl)-1H-pyrazol-4-amine, 2-(4-amino-5-(4,4,5,5-tetramethyl-1,3,2-dioxaborolan-2-yl)-1H-pyrazol-1-yl)ethanol, 2-(4-amino-5-(1,3,2-dioxaborolan-2-yl)-3-methyl-1H-pyrazol-1-yl)ethanol, 1-methyl-5-(5,5-dimethyl-1,3,2-dioxaborinan-2-yl)-1H-pyrazol-4-amine, 1-ethyl-5-(5,5-dimethyl-1,3,2-dioxaborinan-2-yl)-1H-pyrazol-4-amine, 2-(4-amino-5-(5,5-dimethyl-1,3,2-dioxaborinan-2-yl)-1H-pyrazol-1-yl)ethanol, 2-(4-amino-3-methyl-5-(5,5-dimethyl-1,3,2-dioxaborinan-2-yl)-1H-pyrazol-1-yl)ethanol, 1-benzyl-5-(5,5-dimethyl-1,3,2-dioxaborinan-2-yl)-1H-pyrazol-4-amine, and 1-isopropyl-5-(5,5-dimethyl-1,3,2-dioxaborinan-2-yl)-1H-pyrazol-4-amine.

10. Exemplified Compounds of Formula X

Exemplified compounds according to Formula X include, but are not limited to, 4-aminophenylboronic acid, 4-amino-3-methylphenylboronic acid, 4-amino-3-ethylphenylboronic acid, 4-(methylamino)phenylboronic acid, 4-(2-hydroxyethylamino)phenylboronic acid, 4-amino-3-chlorophenylboronic acid, 4-amino-3-methoxyphenylboronic acid, 4-(4,4,5,5-tetramethyl-1,3,2-dioxaborolan-2-yl)benzenamine, 2-methyl-4-(4,4,5,5-tetramethyl-1,3,2-dioxaborolan-2-yl)benzenamine, 4-(1,3,2-dioxaborolan-2-yl)benzenamine, 4-(benzo[d][1,3,2]dioxaborol-2-yl)benzenamine, and 4-(5,5-dimethyl-1,3,2-dioxaborinan-2-yl)benzenamine.

11. Exemplified Compounds of Formula XI

Exemplified compounds according to Formula XI include, but are not limited to, 3-aminopyridin-2-yl-2-boronic acid, 3-(methylamino)pyridin-2-yl-2-boronic acid, 3-amino-5-chloropyridin-2-yl-2-boronic acid, 3-amino-5-methoxypyridin-2-yl-2-boronic acid, 3-(2-hydroxyethylamino)pyridin-2-yl-2-boronic acid, 3-[bis(2-hydroxyethyl)amino]pyridin-2-yl-2-boronic acid, 3-morpholinopyridin-2-yl-2-boronic acid, 3-(pyrrolidin-1-yl)pyridin-2-yl-2-boronic acid, 2-(4,4,5,5-tetramethyl-1,3,2-dioxaborolan-2-yl)pyridin-3-amine, 5-chloro-2-(4,4,5,5-tetramethyl-1,3,2-dioxaborolan-2-yl)pyridin-3-amine, 5-methoxy-2-(4,4,5,5-tetramethyl-1,3,2-dioxaborolan-2-yl)pyridin-3-amine, N-methyl-2-(4,4,5,5-tetramethyl-1,3,2-dioxaborolan-2-yl)pyridin-3-amine, 2-(1,3,2-dioxaborolan-2-yl)pyridin-3-amine, 2-(benzo[d][1,3,2]

dioxaborol-2-yl)pyridin-3-amine, and 2-(5,5-dimethyl-1,3,2-dioxaborinan-2-yl)pyridin-3-amine.

12. Exemplified Compounds of Formula XII

Exemplified compounds according to Formula XII include, but are not limited to, 1H-indol-3-yl-3-boronic acid, 5-amino-1H-indol-3-yl-3-boronic acid, 5,6-dimethoxy-1H-indol-3-yl-3-boronic acid, 5H-[1,3]dioxolo[4,5-f]indol-7-yl-7-boronic acid, 5-amino-1H-indol-3-yl-3-boronic acid, 5-chloro-1H-indol-3-yl-3-boronic acid, 5-methoxy-1H-indol-3-yl-3-boronic acid, 7-methoxy-1H-indol-3-yl-3-boronic acid, 4-fluoro-1H-indol-3-yl-3-boronic acid, 5-bromo-1H-indol-3-yl-3-boronic acid, 4-methyl-1H-indol-3-yl-3-boronic acid, 6-methyl-1H-indol-3-yl-3-boronic acid, 3-(1,3,2-dioxaborolan-2-yl)-1H-indole, 3-(4,4,5,5-tetramethyl-1,3,2-dioxaborolan-2-yl)-1H-indole, 3-(4,5-dimethyl-1,3,2-dioxaborolan-2-yl)-1H-indole, 3-(5,5-dimethyl-1,3,2-dioxaborinan-2-yl)-1H-indole, 3-(benzo[d][1,3,2]dioxaborol-2-yl)-1H-indole, 5-bromo-3-(1,3,2-dioxaborolan-2-yl)-1H-indole, 6-methoxy-3-(4,4,5,5-tetramethyl-1,3,2-dioxaborolan-2-yl)-1H-indole, and 5-methoxy-3-(4,4,5,5-tetramethyl-1,3,2-dioxaborolan-2-yl)-1H-indole.

13. Exemplified Compounds of Formula XIII

Exemplified compounds according to Formula XIII include, but are not limited to, 4-benzoyl-3-hydroxyphenylboronic acid, 4-(3,5-diaminobenzoyl)-3-hydroxyphenylboronic acid, 4-(3,5-dihydroxybenzoyl)-3-hydroxyphenylboronic acid, 4-(2,4-dihydroxybenzoyl)-3-hydroxyphenylboronic acid, 4-(2,4-diaminobenzoyl)-3-hydroxyphenylboronic acid, 4-(2,5-diaminobenzoyl)-3-hydroxyphenylboronic acid, 4-(2,5-dihydroxybenzoyl)-3-hydroxyphenylboronic acid, 4-(2,6-diaminobenzoyl)-3-hydroxyphenylboronic acid, 4-(2,6-dihydroxybenzoyl)-3-hydroxyphenylboronic acid, (4-(1,3,2-dioxaborolan-2-yl)-2-hydroxyphenyl)(phenyl)methanone, (3,5-diaminophenyl)(2-hydroxy-4-(4,4,5,5-tetramethyl-1,3,2-dioxaborolan-2-yl)phenyl)methanone, (4-(1,3,2-dioxaborolan-2-yl)-2-hydroxyphenyl)(3,5-dihydroxyphenyl)methanone, (2-hydroxy-4-(4,4,5,5-tetramethyl-1,3,2-dioxaborolan-2-yl)phenyl)(2,4-dihydroxyphenyl)methanone, (4-(1,3,2-dioxaborolan-2-yl)-2-hydroxyphenyl)(2,4-diaminophenyl)methanone, and (2-hydroxy-4-(5,5-dimethyl-1,3,2-dioxaborinan-2-yl)phenyl)(3,5-dihydroxyphenyl)methanone.

14. Exemplified Compounds of Formula XIV

Exemplified compounds according to Formula XIV include, but are not limited to, 2-benzoyl-3-hydroxyphenylboronic acid, 2-(3,5-diaminobenzoyl)-3-hydroxyphenylboronic acid, 2-(3,5-dihydroxybenzoyl)-3-hydroxyphenylboronic acid, (2-(1,3,2-dioxaborolan-2-yl)-6-hydroxyphenyl)(phenyl)methanone, (3,5-diaminophenyl)(2-hydroxy-6-(4,4,5,5-tetramethyl-1,3,2-dioxaborolan-2-yl)phenyl)methanone, (2-hydroxy-6-(5,5-dimethyl-1,3,2-dioxaborinan-2-yl)phenyl)(3,5-dihydroxyphenyl)methanone, (2,5-diaminophenyl)(2-hydroxy-6-(4,4,5,5-tetramethyl-1,3,2-dioxaborolan-2-yl)phenyl)methanone, and (2-hydroxy-6-(4,4,5,5-tetramethyl-1,3,2-dioxaborolan-2-yl)phenyl)(2,5-dihydroxyphenyl)methanone.

15. Exemplified Compounds of Formula XV

Exemplified compounds according to Formula XV include, but are not limited to, 2,5,6-triaminopyrimidin-4-yl-4-boronic acid, 6-(1,3,2-dioxaborolan-2-yl)pyrimidine-2,4,5-triamine, 6-(4,4,5,5-tetramethyl-1,3,2-dioxaborolan-2-yl)pyrimidine-2,4,5-triamine, 6-(5,5-dimethyl-1,3,2-dioxaborinan-2-yl)pyrimidine-2,4,5-triamine, and 6-(benzo[d][1,3,2]dioxaborol-2-yl)pyrimidine-2,4,5-triamine.

SYNTHESIS EXAMPLES

The following are non-limiting examples of synthesis of boronic acid or boronic ester compounds of the present invention.

Example A

Synthesis of 3-aminophenylboronic acid and 3-hydroxyphenyl boronic acid

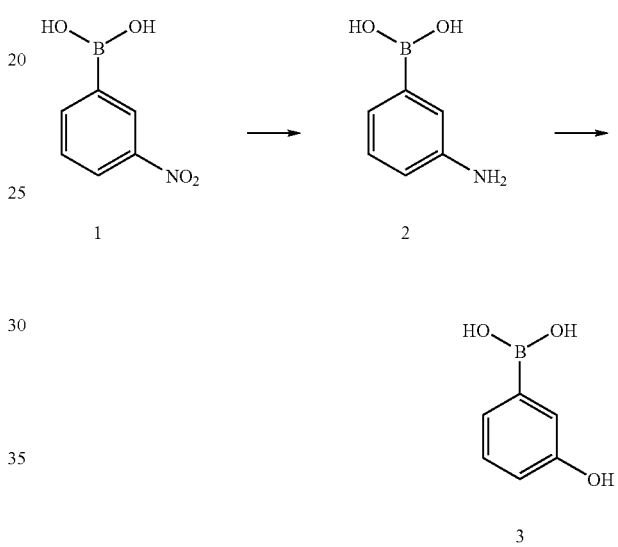

The hydrogenation of m-nitrophenylboronic acid 1 in MeOH-water with platinum oxide ($PtO_2$) at 60 psi hydrogen for 45 min affords 3-aminophenyl boronic acid 2. Compound 2 was converted to 3-hydroxyphenyl boronic acid 3 by diazotization with sodium nitrite/sulfuric acid followed by hydrolysis (Bean, F. R., Johnson, J. R. J. Am. Chem. Soc. 1932, 54, 4415).

Example B

Synthesis of 1-naphthaleneboronic acid

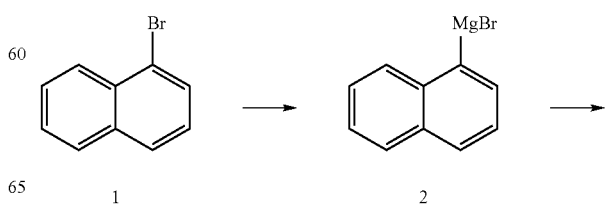

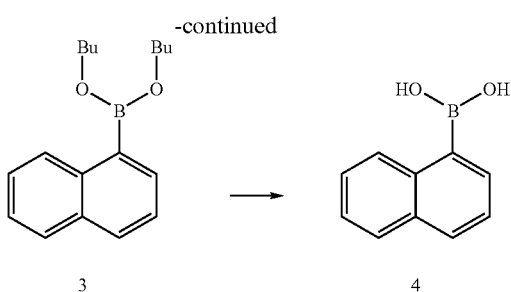

A mixture of 1-bromonaphthalene 1, magnesium powder in THF is irradiated for 15 min to produce Grignard reagent 2 which reacts with tributyl borate to yield the boronic ester 3. Hydrolysis of 3 with aqueous sulfuric acid affords 1-naphthalene boronic acid 4 (Song, Y; Ding, Z; Wang, Q; Tao, F. Syn. Comm. 1998, 28, 3757, WO 9964428).

Example C

Synthesis of 3-(4,4,5,5-tetramethyl-[1,3,2]dioxaborolan-2-yl)phenol

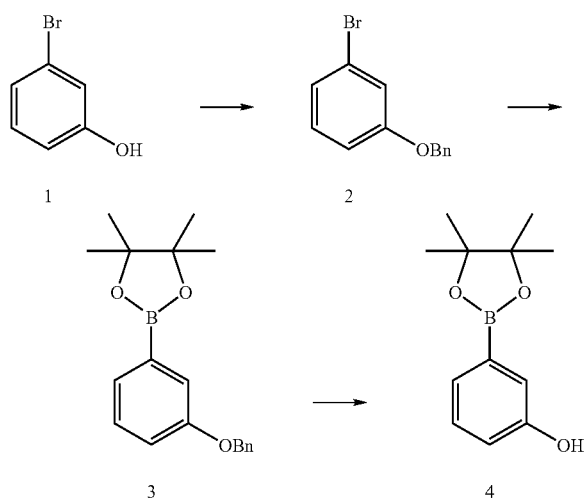

Benzylation of 3-bromophenol 1 with benzyl chloride and potassium carbonate in DMF affords compound 2. Palladium (0)-catalyzed cross-coupling reaction of 2 with bis(pinacolato)diboron, $PdCl_2(dppf)$, and potassium carbonate in DMSO at 80° C. gives rise to compound 3 (Ishiyama, T; Murata, M; Miyaura, N. J. Org. Chem. 1995, 60, 7508). Debenzylation of 3 with Pd/C at 60 psi hydrogen in MeOH produces the target compound 4 (Pennington, T. E.; Kardiman, C; Hutton, C. A. Tetrahedron Lett. 2004, 45, 6657).

B. Auxiliary Developers and Auxiliary Couplers

The compositions for dyeing keratin fibers of the present invention comprise at least one additional keratin dyeing compound selected from auxiliary developers and auxiliary couplers. As used herein, the terms "auxiliary developer" and "auxiliary coupler" respectively refer to any known oxidative keratin dyeing developer (i.e., primary intermediate) compound and any known oxidative keratin dyeing coupler compound, other than those boronic acid or boronic ester compounds of the present invention described above.

1. Auxiliary Developers

Suitable auxiliary developers for use in the compositions described herein include, but are not limited to, p-phenylenediamine derivatives such as: benzene-1,4-diamine (commonly known as p-phenylenediamine), 2-methyl-benzene-1,4-diamine, 2-chloro-benzene-1,4-diamine, 2-thiazole-2-yl-benzene-1,4-diamine, 2-(6-methyl-pyridin-2-yl)-benzene-1,4-diamine, 3'-fluoro-biphenyl-2,5-diamine, 2-propenyl-2-yl-benzene-1,4-diamine, N-phenyl-benzene-1,4-diamine, N-(2-ethoxyethyl)benzene-1,4-diamine, 2-[(4-amino-phenyl)-(2-hydroxy-ethyl)-amino]-ethanol (commonly known as N,N-bis(2-hydroxyethyl)-p-phenylenediamine), (2,5-diamino-phenyl)-methanol, 1-(2'-Hydroxyethyl)-2,5-diaminobenzene, 2-(2,5-diamino-phenyl)-ethanol, N-(4-aminophenyl)benzene-1,4-diamine, 2,6-dimethyl-benzene-1,4-diamine, 2-isopropyl-benzene-1,4-diamine, 1-[(4-aminophenyl)amino]-propan-2-ol, 2-propyl-benzene-1,4-diamine, 1,3-bis[(4-aminophenyl)(2-hydroxyethyl)amino]propan-2-ol, $N^4,N^4$,2-trimethylbenzene-1,4-diamine, 2-methoxy-benzene-1,4-diamine, 1-(2,5-diaminophenyl)ethane-1,2-diol, 2,3-dimethyl-benzene-1,4-diamine, N-(4-amino-3-hydroxy-phenyl)-acetamide, 2,6-diethylbenzene-1,4-diamine, 2,5-dimethylbenzene-1,4-diamine, 2-thien-2-ylbenzene-1,4-diamine, 2-thien-3-ylbenzene-1,4-diamine, 2-pyridin-3-ylbenzene-1,4-diamine, 1,1'-biphenyl-2,5-diamine, 2-(methoxymethyl)benzene-1,4-diamine, 2-(aminomethyl)benzene-1,4-diamine, 2-(2,5-diaminophenoxy)ethanol, N-[2-(2,5-diaminophenoxy)ethyl]-acetamide, N,N-dimethylbenzene-1,4-diamine, N,N-diethylbenzene-1,4-diamine, N,N-dipropylbenzene-1,4-diamine, 2-[(4-aminophenyl)(ethyl)amino]ethanol, 2-[(4-amino-3-methyl-phenyl)-(2-hydroxy-ethyl)-amino]-ethanol, N-(2-methoxyethyl)-benzene-1,4-diamine, 3-[(4-aminophenyl)amino]propan-1-ol, 3-[(4-aminophenyl)-amino]propane-1,2-diol, N-{4-[(4-aminophenyl)amino]butyl}benzene-1,4-diamine, and 2-[2-(2-{2-[(2,5-diaminophenyl)-oxy]ethoxy}ethoxy)ethoxy]benzene-1,4-diamine, 1,3-Bis(N(2-Hydroxyethyl)-N-(4-amino-phenyl)amino)-2-propanol, 2,2'-[1,2-Ethanediyl-bis-(oxy-2,1-ethanediyloxy)]-bis-benzene-1,4-diamine; N,N-Bis(2-hydroxyethyl)-p-phenylinediamine, p-aminophenol derivatives such as: 4-amino-phenol (commonly known as p-aminophenol), 4-methylamino-phenol, 4-amino-3-methyl-phenol, 4-amino-2-hydroxymethyl-phenol, 4-amino-2-methyl-phenol, 4-amino-1-hydroxy-2-(2'-hydroxyethylaminomethyl)benzene, 4-amino-2-methoxymethyl-phenol, 5-amino-2-hydroxy-benzoic acid, 1-(5-amino-2-hydroxy-phenyl)-ethane-1,2-diol, 4-amino-2-(2-hydroxy-ethyl)-phenol, 4-amino-3-(hydroxymethyl)phenol, 4-amino-3-fluoro-phenol, 4-amino-2-(aminomethyl)-phenol, 4-amino-2-fluoro-phenol, 1-hydroxy-2,4-diaminobenzene; 1-(2'-hydroxyethyloxy)-2,4-diaminobenzene, and 2,4-diamino-5-methylphenetol; o-phenylenediamine derivatives such as: 3,4-diaminobenzoic acid and salts thereof; o-aminophenol derivatives such as: 2-amino-phenol (commonly known as o-aminophenol), 2,4-diaminophenol, 2-amino-5-methyl-phenol, 2-amino-6-methyl-phenol, N-(4-amino-3-hydroxy-phenyl)-acetamide, and 2-amino-4-methyl-phenol; and heterocyclic derivatives such as: pyrimidine-2,4,5,6-tetramine (commonly known as 2,4,5,6-tetraaminopyridine), 1-methyl-1H-pyrazole-4,5-diamine, 2-(4,5-diamino-1H-pyrazol-1-yl)ethanol, $N^2,N^2$-dimethylpyridine-2,5-diamine, 2-[(3-amino-6-methoxypyridin-2-yl)amino]ethanol, 6-methoxy-$N^2$-methyl-pyridine-2,3-diamine, 2,5,6-triaminopyrimidin-4(1H)-one, pyridine-2,5-diamine, 1-isopropyl-1H-pyrazole-4,5-diamine, 1-(4-methylbenzyl)-1H-pyrazole-4,5-diamine, 1-(benzyl)-1H-pyrazole-4,5-diamine, 1-(4-chlorobenzyl)-1H-pyrazole-4,5- diamine, pyrazolo[1,5-a]-pyrimidine-3,7-diamine, 5,6,7-trimethylpyrazolo[1,5-a]pyrimidin-3-ylamine hydrochloride, 7-methylpyrazolo[1,5-a]pyrimidin-3-ylamine hydrochloride, 2,5,6,7-teramethyl-pyrazolo[1,5-a]pyrimidin-3-ylamine hydrochloride, 5,7-di-tert-butylpyrazolo[1,5-a]pyrimidin-3-ylamine hydrochloride, 5,7-di-trifluoromethyl-pyrazolo[1,5-a]pyrimidin-3-ylamine hydrochloride, 2-methylpyrazolo[1,5-a]pyrimidin-3,7-diamine hydrochloride, 4-hydroxy-2,5,6-triaminopyrimidine, 1-(2'hydroxyethyl)-amino-3,4-methylene dioxybenzene, and 1-hydroxyethyl-4,5-diaminopyrazole sulphate.

Preferred developers include, but are not limited to: p-phenylenediamine derivatives such as: 2-methyl-benzene-1,4-diamine; benzene-1,4-diamine; 1-(2,5-diamino-phenyl)-ethanol; 2-(2,5-diamino-phenyl)-ethanol; 2-thiazole-2-yl-benzene-1,4-diamine, 2-(6-methyl-pyridin-2-yl)-benzene-1,4-diamine, 3'-fluoro-biphenyl-2,5-diamine, 2-propenyl-2-yl-benzene-1,4-diamine, 2-(methoxymethyl)benzene-1,4-diamine, N-(2-methoxyethyl)benzene-1,4-diamine; 2-[(4-amino-phenyl)-(2-hydroxy-ethyl)-amino]-ethanol; 1-(2,5-diaminophenyl)ethane-1,2-diol; 1-(2'-Hydroxyethyl)-2,5-diaminobenzene; 1,3-Bis(N(2-Hydroxyethyl)-N-(4-aminophenyl)amino)-2-propanol; 2,2'-[1,2-Ethanediyl-bis-(oxy-2,1-ethanediyloxy)]-bis-benzene-1,4-diamine; N,N-Bis(2-hydroxyethyl)-p-phenylinediamine; and mixtures thereof; p-aminophenol derivatives such as: 4-amino-phenol, 4-methylamino-phenol, 4-amino-3-methyl-phenol, 4-amino-2-methoxymethyl-phenol; 1-(5-amino-2-hydroxy-phenyl)-ethane-1,2-diol; 1-Hydroxy-2,4-diaminobenzene; 1-(2'-Hydroxyethyloxy)-2,4-diaminobenzene; 4-Amino-2-aminomethylphenol; 2,4-Diamino-5-methylphenetol; 4-Amino-1-hydroxy-2-(2'-hydroxyethylaminomethyl)benzene; 1-methoxy-2-amino-4-(2'hydroxyethylamino)benzene; 5-aminosalicylic acid and salts thereof; and mixtures thereof; o-phenylenediamine derivatives such as: 3,4-Diaminobenzoic acid and salts thereof; o-aminophenol derivatives such as: 2-amino-phenol, 2-amino-5-methyl-phenol, 2-amino-6-methyl-phenol, N-(4-amino-3-hydroxy-phenyl)-acetamide; 2-amino-4-methyl-phenol; and mixtures thereof; and heterocyclic derivatives such as: pyrimidine-2,4,5,6-tetramine; 1-methyl-1H-pyrazole-4,5-diamine; 2-(4,5-diamino-1H-pyrazol-1-yl)ethanol; 1-(4-methylbenzyl)-1H-pyrazole-4,5-diamine; 1-(benzyl)-1H-pyrazole-4,5-diamine; $N^2,N^2$-dimethyl-pyridine-2,5-diamine; 4-Hydroxy-2,5,6-triaminopyrimidine; 1-(2'hydroxyethyl)-amino-3,4-methylene dioxybenzene; and 1-Hydroxyethyl-4,5-diaminopyrazole sulphate; and mixtures thereof.

More preferred developers include: 2-methyl-benzene-1,4-diamine; benzene-1,4-diamine; 2-thiazole-2-yl-benzene-1,4-diamine, 2-(6-methyl-pyridin-2-yl)-benzene-1,4-diamine, 3'-fluoro-biphenyl-2,5-diamine, 2-propenyl-2-yl-benzene-1,4-diamine, 2-(methoxymethyl)benzene-1,4-diamine, N,N-Bis(2-hydroxyethyl)-p-phenylenediamine; 4-amino-phenol; 4-methylamino-phenol; 4-amino-3-methyl-phenol; 1-Hydroxy-2,4-diaminobenzene; 2-amino-phenol; 2-amino-5-methyl-phenol; 2-amino-6-methyl-phenol; 1-methyl-1H-pyrazole-4,5-diamine; 1-Hydroxyethyl-4,5-diaminopyrazole sulphate; 2-(4,5-diamino-1H-pyrazol-1-yl)ethanol; and mixtures thereof.

2. Auxiliary Couplers

Suitable couplers for use in the compositions described herein include, but are not limited to: phenol, resorcinol, and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, 7-amino-4-hydroxy-naphthalene-2-sulfonic acid, 2-isopropyl-5-methylphenol, 1,2,3,4-tetrahydro-naphthalene-1,5-diol, 2-chloro-benzene-1,3-diol, 4-hydroxy-naphthalene-1-sulfonic acid, benzene-1,2,3-triol, naphthalene-2,3-diol, 5-dichloro-2-methylbenzene-1,3-diol, 4,6-dichlorobenzene-1,3-diol, 2,3-dihydroxy-[1,4]naphthoquinone; and 1-acetoxy-2-methylnaphthalene; m-phenylenediamine derivatives such as: 2,4-diaminophenol, benzene-1,3-diamine, 2-(2,4-diamino-phenoxy)-ethanol, 2-[(3-amino-phenyl)-(2-hydroxy-ethyl)-amino]-ethanol, 2-mehyl-benzene-1,3-diamine, 2-[[2-(2,4-diamino-phenoxy)-ethyl]-(2-hydroxy-ethyl)-amino]-ethanol, 4-{3-[(2,4-diaminophenyl)oxy]propoxy}benzene-1,3-diamine, 2-(2,4-diamino-phenyl)-ethanol, 2-(3-amino-4-methoxy-phenylamino)-ethanol, 4-(2-amino-ethoxy)-benzene-1,3-diamine, (2,4-diaminophenoxy)-acetic acid, 2-[2,4-diamino-5-(2-hydroxy-ethoxy)-phenoxy]-ethanol, 4-ethoxy-6-methyl-benzene-1,3-diamine, 2-(2,4-diamino-5-methyl-phenoxy)-ethanol, 4,6-dimethoxy-benzene-1,3-diamine, 2-[3-(2-hydroxy-ethylamino)-2-methyl-phenylamino]-ethanol, 3-(2,4-diamino-phenoxy)-propan-1-ol, N-[3-(dimethylamino)phenyl]urea, 4-methoxy-6-methylbenzene-1,3-diamine, 4-fluoro-6-methylbenzene-1,3-diamine, 2-({3-[(2-hydroxyethyl)amino]-4,6-dimethoxyphenyl}-amino)ethanol, 3-(2,4-diaminophenoxy)-propane-1,2-diol, 2-[2-amino-4-(methylamino)-phenoxy]ethanol, 2-[(5-amino-2-ethoxy-phenyl)-(2-hydroxy-ethyl)-amino]-ethanol, 2-[(3-aminophenyl)amino]ethanol, 2,4-Diamino-5-(2'-hydroxyethyloxy) toluene; N,N-Dimethyl-3-ureidoaniline; N-(2-aminoethyl) benzene-1,3-diamine, 4-{[(2,4-diamino-phenyl)oxy]methoxy}-benzene-1,3-diamine, 1-methyl-2,6-bis(2-hydroxyethylamino)benzene; and 2,4-dimethoxybenzene-1,3-diamine; m-aminophenols such as: 3-amino-phenol, 2-(3-hydroxy-4-methyl-phenylamino)-acetamide, 2-(3-hydroxyphenylamino)-acetamide, 5-amino-2-methyl-phenol, 5-(2-hydroxy-ethylamino)-2-methyl-phenol, 5-amino-2,4-dichloro-phenol, 3-amino-2-methyl-phenol, 3-amino-2-chloro-6-methyl-phenol, 5-amino-2-(2-hydroxy-ethoxy)-phenol, 2-chloro-5-(2,2,2-trifluoro-ethylamino)-phenol, 5-amino-4-chloro-2-methyl-phenol, 3-cyclopentylamino-phenol, 5-[(2-hydroxyethyl)amino]-4-methoxy-2-methylphenol, 5-amino-4-methoxy-2-methylphenol, 3-(dimethylamino)phenol, 3-(diethylamino)phenol, 5-amino-4-fluoro-2-methylphenol, 5-amino-4-ethoxy-2-methylphenol, 3-amino-2,4-dichloro-phenol, 3-[(2-methoxyethyl)amino]phenol, 3-[(2-hydroxyethyl)amino]phenol, 5-amino-2-ethylphenol, 5-amino-2-methoxyphenol, 5-[(3-hydroxy-propyl)amino]-2-methylphenol, 3-[(3-hydroxy-2-methylphenyl)-amino]propane-1,2-diol, 3-[(2-hydroxyethyl)amino]-2-methylphenol; 1-Methyl-2-hydroxy-4-(2'-hydroxyethyl)amino-benzene; 1,3-Bis-(2,4-Diaminophenoxy)propane; 1-Hydroxy-2-methyl-5-amino-6-chlorobenzene; and heterocyclic derivatives such as: 3,4-dihydro-2H-1,4-benzoxazin-6-ol, 4-methyl-2-phenyl-2,4-dihydro-3H-pyrazol-3-one, 6-methoxyquinolin-8-amine, 4-methylpyridine-2,6-diol, 2,3-dihydro-1,4-benzodioxin-5-ol, 1,3-benzodioxol-5-ol, 2-(1,3-benzodioxol-5-ylamino)ethanol, 3,4-dimethylpyridine-2,6-diol, 5-chloropyridine-2,3-diol, 2,6-dimethoxypyridine-3,5-diamine, 1,3-benzodioxol-5-amine, 2-{ [3,5-diamino-6-(2-hydroxy-ethoxy)-pyridin-2-yl]oxy}-ethanol, 1H-indol-4-ol, 5-amino-2,6-dimethoxypyridin-3-ol, 1H-indole-5,6-diol, 1H-indol-7-ol, 1H-indol-5-ol, 1H-indol-6-ol, 6-bromo-1,3-benzodioxol-5-ol,2-aminopyridin-3-ol, pyridine-2,6-diamine, 3-[(3,5-diaminopyridin-2-yl)oxy]propane-1,2-diol, 5-[(3,5-diaminopyridin-2-yl)oxy]pentane-1,3-diol, 1H-indole-2,3-dione, indoline-5,6-diol, 3,5-dimethoxypyridine-2,6-diamine, 6-methoxypyridine-2,3-diamine; 3,4-dihydro-2H-1,4-benzoxazin-6-amine;

4-hydroxy-N-methylindole, 1H-5-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo-[1,5-a]benzimidazole, 2,6-dihydroxypyridine, 2,6-dihydroxy-3,4-dimethylpyridine, 5-methylpyrazolo[5,1-e]-1,2,3-triazole, 5-methyl-6-chloropyrazolo[5,1-e]-1,2,3,-triazole, 5-phenylpyrazolo[5,1-e]-1,2,3-triazole and its addition salts, 1H-2,6-dimethylpyrazolo[1,5-b]-1,2,4-triazole tosylate, 7,8-dicyano-4-methylimidazolo-[3,2-a]imidazole, 2,7-dimethylpyrazolo[1,5-a]pyrimidin-5-one, 2,5-dimethylpyrazolo[1,5-a]pyrimidin-7-one, and 2-methyl-5-methoxymethyl-pyrazolo[1,5-a]pyrimidin-7-one; 6-Hydroxybenzomorpholine; and 3-Amino-2-methylamino-6-methoxypyridine; and 1-Phenyl-3-methyl-5-pyrazolone-2,4-dihydro-5,2-phenyl-3H-pyrazole-3-one.

Preferred couplers include, but are not limited to: phenol, resorcinol, and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, and 2-isopropyl-5-methylphenol; 1,2,4-Trihydroxybenzene; 1-Acetoxy-2-methylnaphthalene;and mixtures thereof; m-phenylenediamine derivatives such as: benzene-1,3-diamine, 2-(2,4-diamino-phenoxy)-ethanol, 4-{3-[(2,4-diaminophenyl)oxy]propoxy}benzene-1,3-diamine, 2-(3-amino-4-methoxy-phenylamino)-ethanol, 2-[2,4-diamino-5-(2-hydroxy-ethoxy)-phenoxy]-ethanol, and 3-(2,4-diaminophenoxy)-propan-1-ol; 2,4-Diamino-5-(2'-hydroxyethyloxy)toluene; N,N-Dimethyl-3-ureidoaniline; 2,4-Diamino-5-fluorotoluenesulfatehydrate; 1-methyl-2,6-bis(2-hydroxyethylamino)benzene; and mixtures thereof; m-aminophenol derivatives such as: 3-amino-phenol, 5-amino-2-methyl-phenol, 5-(2-hydroxy-ethylamino)-2-methyl-phenol, and 3-amino-2-methyl-phenol; 1-Methyl-2-hydroxy-4-(2'-hydroxyethyl)aminobenzene; 1-Hydroxy-3-amino-2,4-dichlorobenzene; 1,3-Bis-(2,4-Diaminophenoxy)propane; 1-Hydroxy-2-methyl-5-amino-6-chlorobenzene; 5-Amino-4-chloro-2-methylphenol; and mixtures thereof; and heterocyclic derivatives such as: 3,4-dihydro-2H-1,4-benzoxazin-6-ol, 4-methyl-2-phenyl-2,4-dihydro-3H-pyrazol-3-one, 1,3-benzodioxol-5-ol, 1,3-benzodioxol-5-amine, 1H-indol-4-ol, 1H-indole-5,6-diol, 1H-indol-7-ol, 1H-indol-5-ol, 1H-indol-6-ol, 1H-indole-2,3-dione, pyridine-2,6-diamine, 2-aminopyridin-3-ol, 4-hydroxy-N-methylindole, 1H-5-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo-[1,5-a]benzimidazole; 2,6-dihydroxypyridine; 2,6-dihydroxy-3,4-dimethylpyridine; 6-Hydroxybenzomorpholine; 2,6-Dihydroxy-3,4-dimethylpyridine; 3,5-Diamino-2,6-dimethoxypyridine; 3-Amino-2-methylamino-6-methoxypyridine; 1-Phenyl-3-methyl-5-pyrazolone-2,4-dihydro-5,2-phenyl-3H-pyrazole-3-one; and mixtures thereof.

More preferred couplers include: benzene-1,3-diol; 4-chlorobenzene-1,3-diol; 2-methyl-benzene-1,3-diol; benzene-1,3-diamine; 3-amino-phenol; 5-amino-2-methyl-phenol; 1-Methyl-2-hydroxy-4-(2'-hydroxyethyl)aminobenzene; 4-methyl-2-phenyl-2,4-dihydro-3H-pyrazol-3-one; 2-aminopyridin-3-ol; 1-phenyl-3-methylpyrazol-5-one; 1-Phenyl-3-methyl-5-pyrazolone-2,4-dihydro-5,2-phenyl-3H-pyrazole-3-one; and mixtures thereof.

C. Cosmetically Acceptable Medium

The compositions for dyeing keratin fibers of the present invention comprise a cosmetically acceptable medium for the one or more keratin dyeing compounds. The cosmetically acceptable suitable may be selected from water, or a mixture of water and at least one organic solvent to dissolve any compounds which would not typically be sufficiently soluble in water. Suitable organic solvents for use herein include, but are not limited to, C1 to C4 lower alkanols (e.g., ethanol, propanol, isopropanol), aromatic alcohols (e.g., benzyl alcohol and phenoxyethanol); polyols and polyol ethers (e.g., carbitols, 2-butoxyethanol, propylene glycol, propylene glycol monomethyl ether, diethylene glycol monoethyl ether, monomethyl ether, hexylene glycol, glycerol, ethoxy glycol), and propylene carbonate. When present, organic solvents are typically present in an amount ranging from about 1% to about 30% by weight of the composition. Preferred solvents are water, ethanol, propanol, isopropanol, glycerol, 1,2-propylene glycol, hexylene glycol, ethoxy diglycol, and mixtures thereof.

D. Additional Keratin Dyeing Composition Components

The inventive compositions for dyeing keratin fibers comprise at least one boronic acid or boronic ester keratin dyeing compound, at least one additional keratin dyeing compound, and a cosmetically acceptable medium. The inventive compositions may further comprise additional components known, conventionally used, or otherwise effective for use in oxidative dye compositions, including but limited to: direct dyes; oxidizing agents; thickeners; chelants; pH modifiers and buffering agents; carbonate ion sources and radical scavenger systems; anionic, cationic, nonionic, amphoteric or zwitterionic surfactants, or mixtures thereof; anionic, cationic, nonionic, amphoteric or zwitterionic polymers, or mixtures thereof; fragrances; buffers; dispersing agents; peroxide stabilizing agents; natural ingredients, e.g. proteins and protein derivatives, and plant materials (e.g. aloe, chamomile and henna extracts); silicones (volatile or non-volatile, modified or non-modified), film-forming agents, ceramides, preserving agents; and opacifiers.

Some adjuvants referred to above, but not specifically described below, which are suitable are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions) are useful in identifying specific adjuvants to achieve a particular purpose or multipurpose.

1. Direct Dyes

The compositions of the present invention may also comprise compatible direct dyes, in an amount sufficient to provide additional coloring, particularly with regard to intensity. Typically, such an amount will range from 0.05% to 4%, by weight, of the composition. Suitable direct dyes include, but are not limited to: Acid Yellow 1, Acid Orange 3, Disperse Red 17, Basic Brown 17, Acid Black 52, Acid Black 1, Disperse Violet 4,4-Nitro-o-Phenylenediamine, 2-Nitro-p-Phenylenediamine, Picramic Acid, HC Red No. 13, 1,4-Bis-(2'-Hydroxyethyl)-amino-2-nitrobenzene, HC Yellow No. 5, HC Red No. 7, HC Blue No. 2, HC Yellow No. 4, HC Yellow No. 2, HC Orange No. 1, HC Red No. 1, 2-Chloro-5-nitro-N-Hydroxyethyl-p-phenylenediamine, HC Red No. 3, 4-Amino-3-nitrophenol, 2-Hydroxyethylamino-5-nitroanisole, 3-nitro-p-Hydroxyethylaminophenol, 2-amino-3-nitrophenol, 6-nitro-o-toluidine, 3-methylamino-4-nitrophenoxyethanol, 2-nitro-5-glycerymethylanaline, HC Yellow No. 11, HC Violet No. 1, HC Orange No. 2, HC Orange No. 3, HC Yellow No. 9, 4-Nitrophenyl Aminoethylurea, HC Red No. 10, HC Red No. 11, 2-Hydroxyethyl picramic acid, HC Blue No. 12, HC Yellow No. 6, Hydroxyethyl-2-nitro-p-toluidine, HC Yellow No. 12, HC Blue No. 10, HC Yellow No. 7, HC Yellow No. 10, HC Blue No. 9, N-ethyl-3-nitro PABA, 4-amino-2-nitrophenyl-amine-2'-carboxylic acid, 2-chloro-6-ethylamino-4-nitrophenol, 6-Nitro-2,5-pyridinediamine, HC Violet No. 2, 2-amino-6-chloro-4-nitrophenol, 4-hydroxypropylamino-3-nitrophenol, HC Yellow No. 13, 1,2,3,4-Tetrahydro-6-nitrochinoxalin, HC Red No. 14, HC Yellow No. 15, HC Yellow No. 14, 3-Amino-6-methylamino-2-nitropyridine, 2,6-diamino-3-((pyridine-3-yl)azo)pyridine, Basic Red No. 118, Basic Orange No. 69, N-(2-nitro-4-aminophenyl)-allylamine, 4-[(4-Amino-3-methylphenyl)(4-Imino-3-methyl-2,5-Cyclohexadien-1-ylidene) Methyl]-2-Methyl-benzeneamine-Hydrochloride, 1H-Imidazolium,2-[[4-(dimethyl-amino)phenyl]azo]-1,3-dimethylchloride, Pyridinium, 1-methyl-4-[(methylphenyl-hydrazono)methyl]-, methyl sulfate, 1H-Imidazolium, 2-[(4-aminophenyl)azo]-1,3-dimethyl, chloride, Basic Red 22, Basic Red 76, Basic Brown 16, Basic Yellow 57, 7-(2',4'-Dimethyl-5'-sulfophenylazo)-5-sulfo-8-hydroxynaphthalene, Acid Orange 7, Acid Red 33, 1-(3'-Nitro-5'-sulfo-6'-oxophenylazo)-oxonaphthalene chromium complex, Acid Yellow 23, Acid Blue 9, Basic Violet 14, Basic Blue 7, Basic Blue 26, Sodium salt of mixture of mono- & disulfonic acids (mainly the latter) of quinophthlanone or 2-quinolylindandione, Basic Red 2, Basic Blue 99, Disperse Red 15, Acid Violet 43, Disperse Violet 1, Acid Blue 62, Pigment Blue 15, Acid Black 132, Basic Yellow 29, Disperse Black 9, 1-(N-Methylmorpholinium-propylamino)-4-hydroxy-anthraquinone methylsulfate, HC Blue No. 8, HC Red No. 8, HC Green No. 1, HC Red No. 9, 2-Hydroxy-1,4-naphthoquinone, Acid Blue 199, Acid Blue 25, Acid Red 4, Henna Red, Indigo, Cochenille, HC Blue 14, Disperse Blue 23, Disperse Blue 3, Violet 2, Disperse Blue 377, Basic Red 51, Basic Orange 31, Basic Yellow 87, and mixtures thereof. Preferred direct dyes include but are not limited to: Disperse Black 9, HC Yellow 2, HC Yellow 4, HC Yellow 15, 4-nitro-o-phenylenediamine, 2-amino-6-chloro-4-nitrophenol, HC Red 3, Disperse Violet 1, HC Blue 2, Disperse Blue 3, Disperse Blue 377, Basic Red 51, Basic Orange 31, Basic Yellow 87, and mixtures thereof.

2. Oxidizing Agent

The compositions of the present invention may further comprise an oxidizing agent, present in an amount sufficient to bleach melanin pigment in hair and/or to cause formation of dye chromophores from oxidative dye precursors (including developers and/or couplers when present). Typically, such an amount ranges from 1% to 20%, preferably from 3% to 15%, more preferably from 6% to 12%, by weight, of the developer composition. Inorganic peroxygen materials capable of yielding hydrogen peroxide in an aqueous medium are preferred, and include, but are not limited to: hydrogen peroxide; inorganic alkali metal peroxides (e.g., sodium periodate and sodium peroxide); organic peroxides (e.g., urea peroxide, melamine peroxide); inorganic perhydrate salt bleaching compounds (e.g., alkali metal salts of perborates, percarbonates, perphosphates, persilicates, and persulphates, preferably sodium salts thereof), which may be incorporated as monohydrates, tetrahydrates, etc.; alkali metal bromates; enzymes such as laccases and peroxidases; and mixtures thereof. A two electron oxidizing agent, such as alkali ferricyanide, may be used. Preferred is hydrogen peroxide.

3. Thickeners

The compositions of the present invention may additionally comprise a thickener in an amount sufficient to provide the composition with a viscosity so that it can be readily applied to the hair without unduly dripping off the hair and causing mess. Typically, such an amount will be at least 0.1%, preferably at least 0.5%, more preferably, at least 1%, by weight, of the composition.

Preferred for use herein are salt tolerant thickeners, including but not limited to: xanthan, guar, hydroxypropyl guar, scleroglucan, methyl cellulose, ethyl cellulose (available as AQUACOTE(™)), hydroxyethyl cellulose (NATROSOL(™)), carboxymethyl cellulose, hydroxypropylmethyl cellulose, microcrystalline cellulose, hydroxybutylmethyl cellulose, hydroxypropyl cellulose (available as KLUCEL(™)), hydroxyethyl ethyl cellulose, cetyl hydroxyethyl cellulose (available as NATROSOL(™) Plus 330), N-vinylpyrollidone (available as POVIDONE(™)), Acrylates/Ceteth-20 Itaconate Copolymer (available as STRUCTURE (™) 3001), hydroxypropyl starch phosphate (available as STRUCTURE (™) ZEA), polyethoxylated urethanes or polycarbamyl polyglycol ester (e.g. PEG-150/Decyl/SMDI copolymer (available as ACULYN(™) 44), PEG-150/Stearyl/SMDI copolymer available as ACULYN(™) 46), trihydroxystearin (available as THIXCIN(™)), acrylates copolymer (e.g., available as ACULYN(™) 33) or hydrophobically modified acrylate copolymers (e.g., Acrylates/Steareth-20 Methacrylate Copolymer (available as ACULYN(™) 22), non-ionic amphiphilic polymers comprising at least one fatty chain and at least one hydrophilic unit selected from polyether urethanes comprising at least one fatty chain, and blends of Ceteth-10 phosphate, Di-cetyl phosphate and Cetearyl alcohol (available as CRODAFOS(™) CES).

4. Chelants

The compositions of the present invention may also comprise chelants in an amount sufficient to reduce the amount of metals available to interact with formulation components, particularly oxidizing agents, more particularly peroxides. Typically such an amount will range from at least 0.25%, preferably at least 0.5%, by weight, of the composition. Suitable chelants for use herein include but are not limited to: diamine-N,N'-dipolyacid, monoamine monoamide-N,N'-dipolyacid, and N,N'-bis(2-hydroxybenzyl)ethylenediamine-N,N'-diacetic acid chelants (preferably ethylenediaminedisuccinic acid ("EDDS")), carboxylic acids (preferably aminocarboxylic acids), phosphonic acids (preferably aminophosphonic acids) and polyphosphoric acids (in particular straight polyphosphoric acids), their salts and derivatives.

5. pH Modifiers and Buffering Agents

The compositions of the present invention may further comprise a pH modifier and/or buffering agent in an amount that is sufficiently effective to adjust the pH of the composition to fall within a range from 3 to 13, preferably from 8 to 12, more preferably from 9 to 11. Suitable pH modifiers and/or buffering agents for use herein include, but are not limited to: ammonia, alkanolamides such as monoethanolamine, diethanolamine, triethanolamine, monopropanolamine, dipropanolamine, tripropanolamine, tripropanolamine, 2-amino-2-methyl-1-propanol, and 2-amino-2-hydroxymethyl-1,3,-propandiol and guanidium salts, alkali metal and ammonium hydroxides and carbonates, preferably sodium hydroxide and ammonium carbonate, and acidulents such as inorganic and inorganic acids, e.g., phosphoric acid, acetic acid, ascorbic acid, citric acid or tartaric acid, hydrochloric acid, and mixtures thereof.

6. Carbonate Ion Source and Radical Scavenger System

The compositions of the present invention may also comprise a system comprising a source of carbonate ions, carbamate ions, and/or hydrocarbonate ions, and a radical scavenger, in a sufficient amount to reduce damage to the hair during the coloring process. Typically, such an amount will range from 0.1% to 15%, preferably 0.1% to 10%, more preferably 1% to 7%, by weight of the composition, of the carbonate ion, and from 0.1% to 10%, preferably from 1% to 7%, by weight of the composition, of radical scavenger. Preferably, the radical scavenger is present at an amount such that the ratio of radical scavenger to carbonate ion is from 1:1 to 1:4. The radical scavenger is preferably selected such that it is not an identical species as the alkalizing agent.

Suitable sources for the ions include but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Preferred sources of carbonate ions are sodium hydrogen carbonate and potassium hydrogen carbonate. Also preferred are ammonium carbonate, and ammonium hydrogen carbonate.

The radical scavenger is a species that can react with a carbonate radical to convert the carbonate radical by a series of fast reactions to a less reactive species. Preferably, when the radical scavenger comprises an N atom, it has a pKa>7 to prevent the protonation of the nitrogen. Preferred radical scavengers may be selected from the classes of alkanolamines, amino sugars, amino acids and mixtures thereof, and may include, but are not limited to: monoethanolamine, 3-amino-1-propanol, 4-amino-1-butanol,5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, serine, tryptophan and potassium, sodium and ammonium salts of the above and mixtures thereof. Other preferred radical scavenger compounds include benzylamine, glutamic acid, imidazole, di-tert-butylhydroxytoluene, hydroquinone, catechol, and mixtures thereof.

II. Methods of Manufacture

The compositions of this invention may be obtained using conventional methods. A general description of how to make the boronic acid and boronic ester compounds is provided above, along with specific examples of such compounds. The compositions of this invention also may be obtained using conventional methods. The keratin dyeing compositions may be formed as solutions, preferably as aqueous or aqueous-alcohol solutions. The hair dye product compositions may preferably be formed as thick liquids, creams, gels, or emulsions whose composition is a mixture of the dye compound and other dye ingredients with conventional cosmetic additive ingredients suitable for the particular preparation.

III. Methods of Use

The inventive keratin dyeing compositions may be used by admixing them with a suitable oxidizing agent, which reacts with the oxidative dye precursors to develop the hair dye product composition. The oxidizing agent is usually provided in an aqueous composition, which normally is provided as a separate component of the finished keratin dyeing product system and present in a separate container. Upon mixing the keratin dyeing composition, the adjuvants are provided in the hair dye composition as it is applied to the hair to achieve desired product attributes, e.g., pH, viscosity, rheology, etc.

The keratin dyeing composition as it is applied to the hair, can be weakly acidic, neutral or alkaline according to their composition, typically having a pH from 6 to 11, preferably from 7 to 10, more preferably from 8 to 10. The pH of the developer composition is typically acidic, and generally the pH is from 2.5 to 6.5, preferably from 3 to 5. The pH of the hair compositions may be adjusted using a pH modifier as mentioned above.

In order to use the keratin dyeing composition, the above-described compositions are mixed immediately prior to use and a sufficient amount of the mixture is applied to the hair, according to the hair abundance, generally from 60 to 200 grams. Upon such preparation the hair dye composition is applied to the hair to be dyed and remains in contact with the hair for an amount of time effective to dye the hair. Typically, the hair dye composition is allowed to act on the hair for 2 to 60, preferably 15 to 45, more preferably, 30 minutes, at a temperature ranging from 15° C. to 50° C. Thereafter, the hair is rinsed with water, to remove the hair dye composition and dried. If necessary, the hair is washed with a shampoo and rinsed, e.g., with water or a weakly acidic solution, such as a citric acid or tartaric acid solution, and dried. Optionally, a separate conditioning product may also be provided.

Together, components of the keratin dyeing composition form a system for dyeing hair. This system may be provided as a kit comprising in a single package separate containers of the keratin dyeing composition components or other hair treatment product, and instructions for use.

Non-Limiting Examples

The following are non-limiting examples of the compositions of the present invention. The examples are given solely for the purpose of illustration and are not to be construed as limitations of the present invention, as many variations thereof are possible without departing from the spirit and scope of the invention, which would be recognized by one of ordinary skill in the art. In the examples, all concentrations are listed as weight percent, unless otherwise specified.

The following compositions shown in Tables 1 and 3 can be used for oxidatively dyeing hair. The dyeing composition is mixed with an equal weight of a 20-volume hydrogen peroxide solution (i.e., 6% by weight). The resulting mixture is applied to bleached yak hair and permitted to remain in contact with the hair for 30 minutes at 40° C. This dyed hair is then shampooed and rinsed with water and dried. The CIE L*a*b*, C*, and h values are measured by using Minolta Spectrophotometer CM-3700d (as shown in Tables 2 and 4, respectively, for the compositions of Tables 1 and 3).

TABLE 1

Dye Base Ingredients

| Ingredient | Wt % |
| --- | --- |
| Dyes | 0.025 M |
| Sodium sulfite | 0.1 |
| Ascorbic Acid | 0.4 |
| Ethanol | 10.0 |
| Ammonium carbonate | 7.0 |
| EDTA | 0.3 |
| Sodium glycinate | 3.02 |
| Sodium lauryl ether sulfate | 10.0 |
| Deionized Water/KOH to pH = 9 | Q.S to 100 |

TABLE 2
The CIE L*a*b*C*h values obtained by coupling one of 3-hydroxyphenylboronic acid, 3-(4,4,5,5-tetramethyl-[1,3,2]dioxaborolan-2-yl)phenol, and 1-naphthaleneboronic acid with various developers.
| Developer | Coupler | L* | a* | b* | C* | h |
|---|---|---|---|---|---|---|
|  | 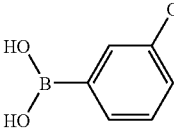 | 33.41 | 4.23 | 14.77 | 15.36 | 74.00 |
| 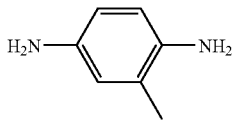 | 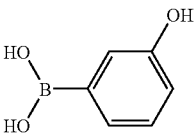 | 44.65 | 2.50 | 20.96 | 21.11 | 83.20 |
| 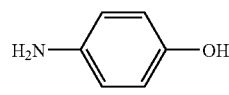 | 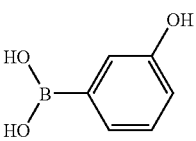 | 59.75 | 1.93 | 14.31 | 14.44 | 82.32 |
| 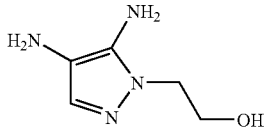 | 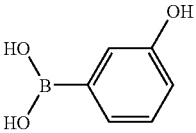 | 53.75 | 24.53 | 10.34 | 26.62 | 22.86 |
|  | 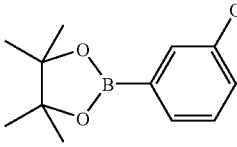 | 33.49 | 4.19 | 15.08 | 15.65 | 74.49 |
| 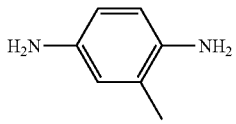 | 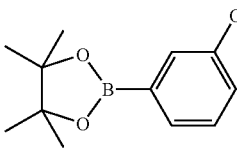 | 44.73 | 1.72 | 20.25 | 20.32 | 85.15 |
| 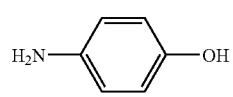 | 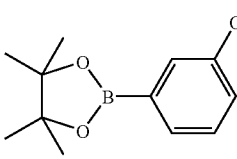 | 60.23 | 2.52 | 16.98 | 17.17 | 81.57 |
| 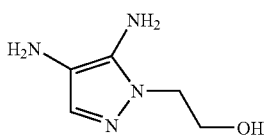 | 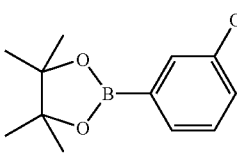 | 50.49 | 19.14 | 7.00 | 20.38 | 20.09 |
| 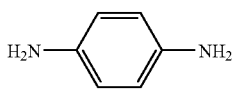 | 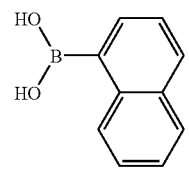 | 27.30 | 9.80 | −14.53 | 17.53 | 303.99 |

TABLE 2-continued

The CIE L*a*b*C*h values obtained by coupling one of 3-hydroxyphenylboronic acid, 3-(4,4,5,5-tetramethyl-[1,3,2]dioxaborolan-2-yl)phenol, and 1-naphthaleneboronic acid with various developers.

| Developer | Coupler | L* | a* | b* | C* | h |
|---|---|---|---|---|---|---|
| 4-aminophenol | 1-naphthaleneboronic acid | 43.12 | 27.85 | 8.02 | 28.98 | 16.06 |
| 4,5-diamino-1-(2-hydroxyethyl)pyrazole | 1-naphthaleneboronic acid | 28.08 | 37.27 | −11.08 | 38.88 | 343.44 |
| N,N-bis(2-hydroxyethyl)-p-phenylenediamine | 1-naphthaleneboronic acid | 30.79 | 2.14 | −29.85 | 29.93 | 274.09 |
| 4-aminophenol | indol-4-ylboronic acid | 34.48 | 27.28 | 11.54 | 29.63 | 22.93 |
| p-phenylenediamine | indol-4-ylboronic acid | 20.46 | 8.81 | −8.65 | 12.34 | 315.52 |
| 4,5-diamino-1-(2-hydroxyethyl)pyrazole | indol-4-ylboronic acid | 24.83 | 32.63 | −6.82 | 33.33 | 348.19 |
| N,N-bis(2-hydroxyethyl)-p-phenylenediamine | indol-4-ylboronic acid | 24.07 | 2.07 | −24.04 | 24.13 | 274.91 |
| 4-aminophenol | 3-(dimethylamino)phenylboronic acid | 60.09 | 4.55 | 17.62 | 18.20 | 75.53 |

TABLE 2-continued

The CIE L\*a\*b\*C\*h values obtained by coupling one of 3-hydroxyphenylboronic acid,
3-(4,4,5,5-tetramethyl-[1,3,2]dioxaborolan-2-yl)phenol, and 1-naphthaleneboronic acid with
various developers.

| Developer | Coupler | L\* | a\* | b\* | C\* | h |
|---|---|---|---|---|---|---|
| H₂N–C₆H₄–NH (p-phenylenediamine) | 3-(N,N-dimethylamino)phenylboronic acid | 34.55 | 5.71 | 8.65 | 10.37 | 56.57 |
| 4,5-diamino-1-(2-hydroxyethyl)pyrazole | 3-(N,N-dimethylamino)phenylboronic acid | 39.22 | 33.86 | −2.55 | 33.95 | 355.70 |
| N,N-bis(2-hydroxyethyl)-p-phenylenediamine | 3-(N,N-dimethylamino)phenylboronic acid | 45.50 | −3.13 | −2.05 | 3.74 | 213.21 |
| Untreated hair | | 71.19 | −0.39 | 3.43 | 3.45 | 96.48 |

TABLE 3

Dye Base Ingredients

| Ingredient | Wt % |
|---|---|
| Dyes | 0.025 M |
| Sodium sulfite | 0.1 |
| Ascorbic Acid | 0.4 |
| Ethanol | 10.0 |
| EDTA | 0.3 |
| Ammonium hydroxide | 9.0 |
| Sodium lauryl ether sulfate | 10.0 |
| Deionized Water | Q.S to 100 |

TABLE 4

The CIE L\*a\*b\*C\*h values obtained by coupling one of 3-hydroxyphenylboronic acid,
3-(4,4,5,5-tetramethyl-[1,3,2]dioxaborolan-2-yl)phenol, and 1-naphthaleneboronic acid with
various developers.

| Developer | Coupler | L\* | a\* | b\* | C\* | h |
|---|---|---|---|---|---|---|
| p-phenylenediamine | 3-hydroxyphenylboronic acid | 34.08 | 4.73 | 14.25 | 15.01 | 71.63 |
| 2-methyl-p-phenylenediamine | 3-hydroxyphenylboronic acid | 41.60 | 4.33 | 17.26 | 17.79 | 75.91 |

TABLE 4-continued

The CIE L*a*b*C*h values obtained by coupling one of 3-hydroxyphenylboronic acid, 3-(4,4,5,5-tetramethyl-[1,3,2]dioxaborolan-2-yl)phenol, and 1-naphthaleneboronic acid with various developers.

| Developer | Coupler | L* | a* | b* | C* | h |
|---|---|---|---|---|---|---|
| 4-aminophenol | 3-hydroxyphenylboronic acid | 62.99 | 1.59 | 19.42 | 19.49 | 85.32 |
| 4,5-diamino-1-(2-hydroxyethyl)pyrazole | 3-hydroxyphenylboronic acid | 47.46 | 26.50 | 6.50 | 27.29 | 13.78 |
| 1,4-phenylenediamine | 3-(4,4,5,5-tetramethyl-[1,3,2]dioxaborolan-2-yl)phenol | 34.15 | 4.90 | 13.63 | 14.49 | 70.22 |
| 2-methyl-1,4-phenylenediamine | 3-(4,4,5,5-tetramethyl-[1,3,2]dioxaborolan-2-yl)phenol | 42.54 | 4.43 | 17.12 | 17.68 | 75.48 |
| 4-aminophenol | 3-(4,4,5,5-tetramethyl-[1,3,2]dioxaborolan-2-yl)phenol | 64.03 | 2.46 | 20.64 | 20.79 | 83.20 |
| 4,5-diamino-1-(2-hydroxyethyl)pyrazole | 3-(4,4,5,5-tetramethyl-[1,3,2]dioxaborolan-2-yl)phenol | 48.02 | 26.76 | 6.49 | 27.54 | 13.64 |
| 1,4-phenylenediamine | 1-naphthaleneboronic acid | 20.04 | 8.29 | −11.80 | 14.42 | 305.11 |
| 4,5-diamino-1-(2-hydroxyethyl)pyrazole | 1-naphthaleneboronic acid | 21.08 | 27.05 | −4.85 | 27.48 | 349.82 |

TABLE 4-continued

The CIE L*a*b*C*h values obtained by coupling one of 3-hydroxyphenylboronic acid, 3-(4,4,5,5-tetramethyl-[1,3,2]dioxaborolan-2-yl)phenol, and 1-naphthaleneboronic acid with various developers.

| Developer | Coupler | L* | a* | b* | C* | h |
|---|---|---|---|---|---|---|
| 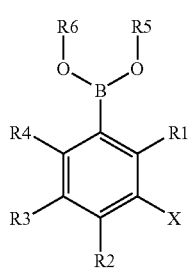 | | 22.39 | 8.38 | −29.83 | 30.98 | 285.69 |
| Untreated hair | | 71.19 | −0.39 | 3.43 | 3.45 | 96.48 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition for dyeing keratin fibers, said composition comprising:
(a) at least one keratin dyeing compound selected from aromatic systems which comprise at least one boronic acid or boronic ester moiety and which are capable of forming upon oxidation a nucleophile or an electrophile, wherein said aromatic system which comprises at least one boronic acid or boronic ester moiety and which is capable of forming upon oxidation a nucleophile or an electrophile is selected from a compound according to one of the following formulas I to XV:

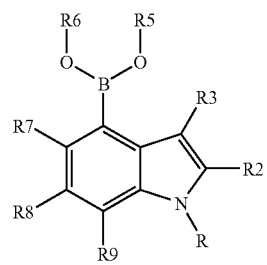

I

-continued

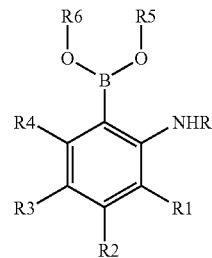

II

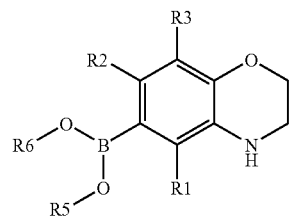

III

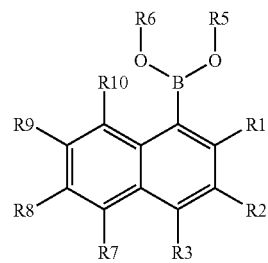

IV

V

-continued

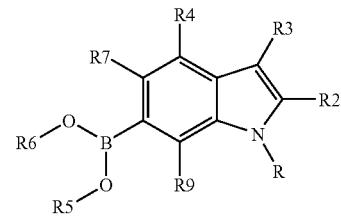
VI

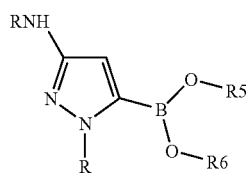
VIII

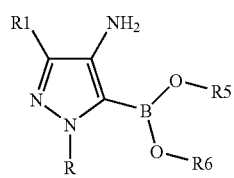
iX

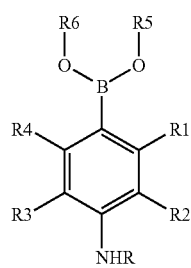
X

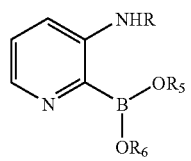
XI

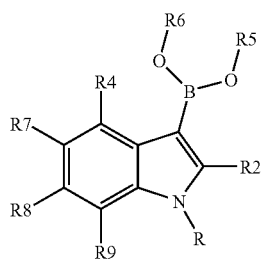
XII

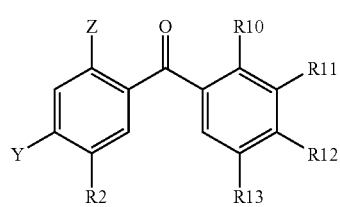
XIII

-continued

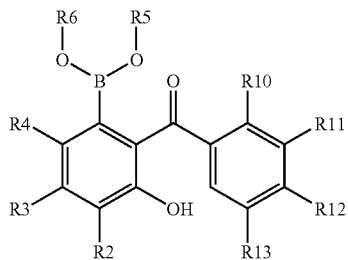
XIV

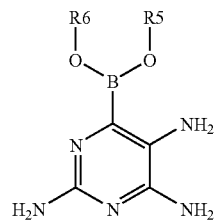
XV wherein R1, R2, R3, R4, R7, R8, R9, R10, R11, R12, and R13 each are independently selected from the group consisting of a hydrogen atom; a halogen atom; an amino radical, a hydroxyl radical; a cyano radical; a $C_1$-$C_4$ alkyl radical; a trifluoromethyl radical, an alkylamino radical; a hydroxyalkylamino radical; an acetylamido radical; a carboxyl radical; an alkoxy radical; an alkoxyalkyl radical; a carbamoyl radical; an alkylcarbamoylradical; a hydroxyalkylcarbamoyl radical; an amido radical; an alkylamido radical; an alkylcarbonyl radical; an alkoxycarbonyl radical; an aryloxy radical; an acyloxy radical; an alkylthio radical; an arylthio radical; a heteroarylthio radical; a heteroaryloxy radical; a 5- or 6-membered heterocycle having at least one heteroatom selected from nitrogen, oxygen, or sulfur and being optionally substituted; an aryl radical which is optionally substituted; a sulfonyl radical; a sulfinyl radical; a phosphonyl radical; a sulfamoyl radical; a siloxy radical; an acyloxy radical; a carbamoyloxy radical; a sulphonamide radical; an imide radical; a ureido radical; a sulfamoylamino radical; an alkoxycarbonylamino radical; an aryloxycarbonylamino radical; an aryloxycarbonyl radical; and a benzenesulfonamido radical;

wherein R is selected group consisting of hydrogen, COR 1, and C-linked monovalent substituents selected from the group consisting of:
  (i) substituted or unsubstituted, straight or branched, alkyl, mono- or poly-unsaturated alkyl, heteroalkyl, aliphatic, heteroaliphatic, or heteroolefinic systems,
  (ii) substituted or unsubstituted, mono- or poly-cyclic aliphatic, aryl, or heterocyclic systems, and
  (iii) substituted or unsubstituted, mono-, poly-hydroxy or -fluoro alkyl systems; wherein said systems of (i), (ii) and (iii) comprise from about 1 to about 10 carbon atoms and from about 0 to about 5 heteroatoms selected from the group consisting of O, S, N, P, and Si;

wherein R5 and R6 each are independently selected from the group consisting of hydrogen and lower alkyl groups which can be joined together as a straight or branched alkylene chain forming a five or six-membered ring or an aromatic ring;

wherein X is selected from the group consisting of hydroxyl, B(OR5)OR6, and NA1A2;

wherein Y and Z each are independently selected from the group consisting of hydroxyl and B(OR5)OR6, provided that at least one of which is B(OR5)OR6; and wherein $A^1$ and $A^2$ are monovalent and are independently selected from the group consisting of hydrogen; substituted or unsubstituted, straight or branched, alkyl, mono- or poly-unsaturated alkyl, heteroalkyl, aliphatic, heteroaliphatic, or heteroolefinic systems; substituted or unsubstituted, mono- or polycyclic aliphatic, aryl, or heterocyclic systems; and substituted or unsubstituted, mono-, poly-, per-fluoro alkyl systems; or $A^1$ and $A^2$ together with a nitrogen atom to which they are bound form a ring; wherein all of said systems comprise from about 1 to about 10 carbon atoms and from about 0 to about 5 heteroatoms selected from the group consisting of O, S, N, P, and Si;

(b) at least one additional keratin dyeing compound selected from the group consisting of auxiliary developers and auxiliary couplers; and (c) a cosmetically suitable medium.

2. A composition according to claim 1, wherein said aromatic system which comprises at least one boronic acid or boronic ester moiety and which is capable of forming upon oxidation a nucleophile or an electrophile is selected from the group consisting of 3-hydroxyphenylboronic acid, 3-hydroxy-2-methylphenylboronic acid, 2-chloro-5-hydroxyphenylboronic acid, 6-chloro-3-hydroxy-2-methylphenylboronic acid, 3-hydroxy-6-methoxy-2-methyiphenylboronic acid, 3-hydroxy-2,4-dimethylphenylboronic acid, 2-ethyl-3-hydroxyphenylboronic acid, 3-hydroxy-2-(2-hydroxyethyl)phenylboronic acid, 2-(2,2,2-trifluoroethyl)-3-hydroxyphenylboronic acid, 2-(cyanomethyl)-3-hydroxyphenylboronic acid, 3-(4,4,5,5-tetramethyl-1,3,2-dioxaborolan-2-yl)phenol, 2-methyl-3-(4,4,5,5-tetramethyl-1,3,2-dioxaborolan-2-yl)phenol, 4-chloro-3-(4,4,5,5-tetramethyl-1,3,2-dioxaborolan-2-yl)phenol, 4-chloro-2-methyl-3-(4,4,5,5-tetramethyl-1,3,2-dioxaborolan-2-yl)phenol, 4-methoxy-2-methyl-3-(4,4,5,5-tetramethyl-1,3,2-dioxaborolan-2-yl)phenol, 2,6-dimethyl-3-(4,4,5,5-tetramethyl-1,3,2-dioxaborolan-2-yl)phenol, 2-ethyl-3-(4,4,5,5-tetramethyl-1,3,2-dioxaborolan-2-yl)phenol, 2-(2-hydroxyethyl)-3-(4,4,5,5-tetramethyl-1,3,2-dioxaborolan-2-yl)phenol, 3-(5,5-dimethyl-1,3,2-dioxaborinan-2-yl)phenol, 2-methyl-3-(5,5-dimethyl-1,3,2-dioxaborinan-2-yl)phenol, 3-(benzo[d][1,3,2]dioxaborol-2-yl)phenol, 3-(benzo[d][1,3,2]dioxaborol-2-yl)-2-methylphenol, 3-(1,3,2-dioxaborolan-2-yl)phenol, 3-(1,3,2-dioxaborolan-2-yl)-2-methylphenol, 3-aminophenylboronic acid, 3-amino-2-methylphenylboronic acid, 3-(methylamino)phenylboronic acid, 3-(2-hydroxyethylamino)phenylboronic acid, 3-[bis(2-hydroxyethyl)amino]phenylboronic acid, 3-morpholinophenylboronic acid, 3-(pyrrolidin-1-yl)phenylboronic acid, 3-amino-4-chlorophenylboronic acid, 5-amino-2,4-dichlorophenylboronic acid, 5-amino-2-methoxyphenylboronic acid, 3-amino-4-methoxyphenylboronic acid, 3-(4,4,5,5-tetramethyl-1,3,2-dioxaborolan-2-yl)benzenamine, 3-(5,5-dimethyl-1,3,2-dioxaborinan-2-yl)benzenamine, 3(1,3,2-dioxaborolan-2yl)benzenamine, and 3-(benzo[d][1,3,2]dioxaborol-2-yl)benzenamine.

3. A composition according to claim 1, wherein said aromatic system which comprises at least one boronic acid or boronic ester moiety and which is capable of forming upon oxidation a nucleophile or an electrophile is selected from the group consisting of 2-aminophenylboronic acid, 2-amino-5-methylphenylboronic acid, 2-amino-5-ethylphenylboronic acid, 2-amino-4-chlorophenylboronic acid, 2-amino-4-methoxyphenylboronic acid, 2-(2-hydroxyethylamino)phenylboronic acid, 2-[bis(2-hydroxyethyl)amino]phenylboronic acid, 2-morpholinophenylboronic acid, 2-(pyrrolidin-1-yl)phenylboronic acid, 2-(methylamino)phenylboronic acid, 2-(4,4,5,5-tetramethyl-1,3,2-dioxaborolan-2-yl)benzenamine, 4-methyl-2-(4,4,5,5-tetramethyl-1,3,2-dioxaborolan-2-yl)benzenamine, 2-(1,3,2-dioxaborolan-2-yl)benzenamine, 2-(benzo[d][1,3,2]dioxaborol-2-yl)benzenamine, and 2-(5,5-dimethyl-1,3 ,2-dioxaborinan-2-yl)benzenamine.

4. A composition according to claim 1, wherein said aromatic system which comprises at least one boronic acid or boronic ester moiety and which is capable of forming upon oxidation a nucleophile or an electrophile is selected from the group consisting of 3,4-dihydro-2H-benzo [b][1,4]oxazin-6-yl-6-boronic acid, 3,4-dihydro-7-methyl-2H-benzo[b][1,4]oxazin-6-yl-6-boronic acid, 7-ethyl-3,4-dihydro-2H-benzo[b][1,4]oxazin-6-yl-6-boronic acid, 3,4-dihydro-7-methoxy-2H-benzo[b][1,4]oxazin-6-yl-6-boronic acid, 6-(1,3,2-dioxaborolan-2-yl)-3,4-dihydro-2H-benzo[b][1,4]oxazine, 6-(benzo[d][1,3,2]dioxaborol-2-yl)-3,4-dihydro-2H-benzo [b][1,4]oxazine, and 3,4-dihydro-6-(5,5-dimethyl-1,3,2-dioxaborinan-2-yl)-2H-benzo[b][1,4]oxazine.

5. A composition according to claim 1, wherein said aromatic system which comprises at least one boronic acid or boronic ester moiety and which is capable of forming upon oxidation a nucleophile or an electrophile is selected from the group consisting of naphthalen-1-yl-1-boronic acid, 2-methylnaphthalen-1-yl-1-boronic acid, 2-ethylnaphthalen-1-yl-1-boronic acid, 4-chloronaphthalen-1-yl-1-boronic acid, 4-methoxynaphthalen-1-yl-1-boronic acid, 4,4,5,5-tetramethyl-2-(naphthalen-4-yl)-1,3,2-dioxaborolane, 4,4,5,5-tetramethyl-2-(2-methylnaphthalen-1-yl)-1,3,2-dioxaborolane, 2-(naphthalen-4-yl)-1,3,2-dioxaborolane ,2-(naphthalen-4-yl)benzo[d][1,3,2]dioxaborole, 5,5-dimethyl-2-(naphthalen-4-yl)-,3,2-dioxaborinane, 7-methylnaphthalen-1-yl-1-boronic acid, 6-methylnaphthalen-1-yl-1-boronic acid, 8-methylnaphthalen-1-yl-1-boronic acid, 2-(2,2,2-trifluoroethyl)naphthalen-1-yl-1-boronic acid, and 2-(2-hydroxyethyl)naphthalen-1-yl-1-boronic acid.

6. A composition according to claim 1, wherein said aromatic system which comprises at least one boronic acid or boronic ester moiety and which is capable of forming upon oxidation a nucleophile or an electrophile is selected from the group consisting of 1H-indol-4-yl-4-boronic acid, 7-chloro-1H-indol-4-yl-4-boronic acid, 7-methoxy-1H-indol-4-yl-4-boronic acid, 2-methyl-1H-indol-4-yl-4-boronic acid, 2,3-dimethyl-1H-indol-4-yl-4-boronic acid, 5-methyl-1H-indol-4-yl-4-boronic acid, 1-methyl-1H-indol-4-yl-4-boronic acid, 4-(4,4,5,5-tetramethyl-1,3,2-dioxaborolan-2-yl)-1H-indole, 4-(1,3,2-dioxaborolan-2-yl)-1H-indole, 4-(benzo[d][1,3,2]dioxaborol-2-yl)-1H-indole, and 4-(5,5-dimethyl-1,3,2-dioxaborinan-2-yl)-1H-indole.

7. A composition according to claim 1, wherein said aromatic system which comprises at least one boronic acid or boronic ester moiety and which is capable of forming upon oxidation a nucleophile or an electrophile is selected from the group consisting of 1H-indol-6-yl-6-boronic acid, 2-methyl-1H-indol-6-yl-6-boronic acid, 2,3-dimethyl-1H-indol-6-yl-6-boronic acid, 7-methyl-1H-indol-6-yl-6-boronic acid, 1-methyl-1H-indol-6-yl-6-boronic acid, 5-chloro-1H-indol-6-yl-6-boronic acid, 5-methoxy-1H-indol-6-yl-6-boronic acid, 6-(4,4,5,5-tetramethyl-1,3,2-dioxaborolan-2-yl)-1H-indole, 6-(1,3,2-dioxaborolan-2-yl)-1H-indole, 6-(benzo[d]

[1,3,2]dioxaborol-2-yl)-1H-indole, and 6-(5,5-dimethyl-1,3,2-dioxaborinan-2-yl)-1H-indole.

8. A composition according to claim 1, wherein said aromatic system which comprises at least one boronic acid or boronic ester moiety and which is capable of forming upon oxidation a nucleophile or an electrophile is selected from the group consisting of 5-hydroxy-1H-indol-6-yl-6-boronic acid, 6-hydroxy-1H-indol-5-yl-5-boronic acid, 5-hydroxy-2-methyl-1H-indol-6-yl-6-boronic acid, 6-hydroxy-2-methyl-1H-indol-5-yl-5-boronic acid, 5-hydroxy-2,3-dimethyl-1H-indol-6-yl-6-boronic acid, 6-hydroxy-2,3-dimethyl-1H-indol-5-yl-5-boronic acid, 5-hydroxy-1-methyl-1H-indol-6-yl-6-boronic acid, 6-hydroxy-1-methyl-1H-indol-5-yl-5-boronic acid, 5-hydroxy-1-(2-hydroxyethyl)-1H-indol-6-yl-6-boronic acid, 6-hydroxy-1-(2-hydroxyethyl)-1H-indol-5-yl-5-boronic acid, 6-(4,4,5,5-tetramethyl-1,3,2-dioxaborolan-2-yl)-1H-indol-5-ol, 5-(4,4,5,5-tetramethyl-1,3,2-dioxaborolan-2-yl)-1H-indol-6-ol, 6-(1,3,2-dioxaboroian-2-yl)-1H-indol-5-ol, 5-(5,5-dimethyl-1,3,2-dioxaborinan-2-yl)-1H-indol-6-ol, 2-methyl-6-(4,4,5,5-tetramethyl-1,3,2-dioxaboroian-2-yl)-1H-indol-5-ol, and 2-methyl-5-(4,4,5,5-tetramethyl-1,3,2-dioxaborolan-2-yl)-1H-indol-6-ol.

9. A composition according to claim 1, wherein said aromatic system which comprises at least one boronic acid or boronic ester moiety and which is capable of forming upon oxidation a nucleophile or an electrophile is selected from the group consisting of 1-ethyl-3-(methylamino)-1H-pyrazol-5-yl-5-boronic acid, 1-(2-hydroxyethyl)-3-(methylamino)-1H-pyrazol-5-yl-5-boronic acid, 3-acetamido-1-(2-hydroxyethyl)-1H-pyrazol-5-yl-5-boronic acid, 3-(2-hydroxyethylamino)-1-(2-hydroxyethyl)-1H-pyrazol-5-yl-5-boronic acid, 1-methyl-3-(methylamino)-1H-pyrazol-5-yl-5-boronic acid, 5-(1,3,2-dioxaborolan-2-yl)-N,1-dimethyl-1H-pyrazol-3-amine, 2-(3-(ethylamino)-5-(4,4,5,5-tetramethyl-1,3,2-dioxaborolan-2-yl)-1H-pyrazol-1-yl)ethanol, N-(1-(2-hydroxyethyl)-5-(5,5-dimethyl-1,3,2-dioxaborinan-2-yl)-1H-pyrazol-3-yl)acetamide, 3-amino-1-phenyl-1H-pyrazol-5-yl-5-boronic acid, and N-(5-(benzo[d][1,3,2]dioxaborol-2-yl)-1-(2-hydroxyethyl)-1H-pyrazol-3-yl)acetamide.

10. A composition according to claim 1, wherein said aromatic system which comprises at least one boronic acid or boronic ester moiety and which is capable of forming upon oxidation a nucleophile or an electrophile is selected from the group consisting of 4-amino-1-methyl-1H-pyrazol-5-yl-5-boronic acid, 4-amino-1-ethyl-1H-pyrazol-5-yl-5-boronic acid, 4-amino-1-(2-hydroxyethyl)-1H-pyrazol-5-yl-5-boronic acid, 4-amino-1-(2-hydroxyethyl)-3-methyl-1H-pyrazol-5-yl-5-boronic acid, 4-amino-1-benzyl-1H-pyrazol-5-yl-5-boronic acid, 4-amino-1-isopropyl-1H-pyrazol-5-yl-5-boronic acid, 5-(1,3,2-dioxaborolan-2-yl)-1-methyl-1H-pyrazol-4-amine, 5-(1,3,2-dioxaborolan-2-yl)-1-ethyl-1H-pyrazol-4-amine, 2-(4-amino-5-(1,3,2-dioxaborolan-2-yl)-1H-pyrazol-1-yl)ethanol, 2-(4-amino-5-(1,3,2-dioxaborolan-2-yl)-3-methyl-1H-pyrazol-1-yl)ethanol, 1-benzyl-5-(1,3,2-dioxaborolan-2-yl)-1H-pyrazol-4-amine, 5-(1,3,2-dioxaborolan-2-yl)-1-isopropyl-1H-pyrazol-4-amine, 1-methyl-5-(4,4,5,5-tetramethyl-1,3,2-dioxaborolan-2-yl)-1H-pyrazol-4-amine, 1-ethyl-5-(4,4,5,5-tetramethyl-1,3,2-dioxaborolan-2-yl)-1H-pyrazol-4-amine, 2-(4-amino-5-(4,4,5,5-tetramethyl-1,3,2-dioxaborolan-2-yl)-1H-pyrazol-1-yl)ethanol, 2-(4-amino-5-(1,3,2-dioxaborolan-2-yl)-3-methyl-1H-pyrazol-1-yl)ethanol, 1-methyl-5-(5,5-dimethyl-1,3,2-dioxaborinan-2-yl)-1H-pyrazol-4-amine, 1-ethyl-5-(5,5-dimethyl-1,3,2-dioxaborinan-2-yl)-1H-pyrazol-4-amine, 2-(4-amino-5-(5,5-dimethyl-,1,3,2-dioxaborinan-2-yl)-1H-pyrazol-1-yl)ethanol, 2-(4-amino-3-methyl-5-(5,5-dimethyl-1,3,2-dioxaborinan-2-yl)-1H-pyrazol-1-yl)ethanol, 1-benzyl-5-(5,5-dimethyl-1,3,2-dioxaborinan-2-yl)-1H-pyrazol-4-amine, and 1-isopropyl-5-(5,5-dimethyl-1,3,2-dioxaborinan-2-yl)-1H-pyrazol-4-amine.

11. A composition according to claim 1, wherein said aromatic system which comprises at least one boronic acid or boronic ester moiety and which is capable of forming upon oxidation a nucleophile or an electrophile is selected from the group consisting of 4-aminophenylboronic acid, 4-amino-3-methyiphenylboronic acid, 4-amino-3-ethylphenylboronic acid, 4-(methylamino)phenylboronic acid, 4-(2-hydroxyethylamino)phenylboronic acid, 4-amino-3-chlorophenylboronic acid, 4-amino-3-methoxyphenylboronic acid, 4-(4,4,5,5-tetramethyl-1,3,2-dioxaborolan-2-yl)benzenamine, 2-methyl-4-(4,4,5,5-tetramethyl-1,3,2-dioxaborolan-2-yl)benzenamine, 4-(1,3,2-dioxaborolan-2-yl)benzenamine, 4-(benzo[d][1,3,2]dioxaborol-2-yl)benzenamine, and 4-(5,5-dimethyl-1,3,2-dioxaborinan-2-yl)benzenamine.

12. A composition according to claim 1, wherein said aromatic system which comprises at least one boronic acid or boronic ester moiety and which is capable of forming upon oxidation a nucleophile or an electrophile is selected from the group consisting of 3-aminopyridin-2-yl-2-boronic acid, 3-(methylamino)pyridin-2-yl-2-boronic acid, 3-amino-5-chloropyridin-2-yl-2-boronic acid, 3-amino-5-methoxypyridin-2-yl-2-boronic acid, 3-(2-hydroxyethylamino)pyridin-2-yl-2-boronic acid, 3-[bis(2-hydroxyethyl)amino]pyridin-2-yl-2-boronic acid, 3-morpholinopyridin-2-yl-2-boronic acid, 3-(pyrrolidin-1-yl)pyridin-2-yl-2-boronic acid, 2-(4,4,5,5-tetramethyl-1,3,2-dioxaborolan-2-yl)pyridin-3-amine, 5-chloro-2-(4,4,5,5-tetramethyl-1,3,2-dioxaborolan-2-yl)pyridin-3-amine, 5-methoxy-2-(4,4,5,5-tetramethyl-1,3,2-dioxaborolan-2-yl)pyridin-3-amine, N-methyl-2-(4,4,5,5-tetramethyl-1,3,2-dioxaborolan-2-yl)pyridin-3-amine, 2-(1,3,2-dioxaborolan-2-yl)pyridin-3-amine, 2-(benzo[d][1,3,2]dioxaborol-2-yl)pyridin-3-amine, and 2-(5,5-dimethyl-1,3,2-dioxaborinan-2-yl)pyridin-3-amine.

13. A composition according to claim 1, wherein said aromatic system which comprises at least one boronic acid or boronic ester moiety and which is capable of forming upon oxidation a nucleophile or an electrophile is selected from the group consisting of 1H-indol-3-yl-3-boronic acid, 5-amino-1H-indol-3-yl-3-boronic acid, 5,6-dimethoxy-1H-indol-3-yl-3-boronic acid, 5H-[1,3]dioxolo[4,5-f]indol-7-yl-7-boronic acid, 5-amino-1H-indol-3-yl-3-boronic acid, 5-chloro-1H-indol-3-yl-3-boronic acid, 5-methoxy-1H-indol-3-yl-3-boronic acid, 7-methoxy-1H-indol-3-yl-3-boronic acid, 4-fluoro-1H-indol-3-yl-3-boronic acid, 5-bromo-1H-indol-3-yl-3-boronic acid, 4-methyl-1H-indol-3-yl-3-boronic acid, 6-methyl-1H-indol-3-yl-3-boronic acid, 3-(1,3,2-dioxaborolan-2-yl)-1H-indole, 3-(4,4,5,5-tetramethyl-1,3,2-dioxaborolan-2-yl)-1H-indole, 3-(4,5-dimethyl-1,3,2-dioxaborolan-2-yl)-1H-indole, 3-(5,5-dimethyl-1,3,2-dioxaborinan-2-yl)-1H-indole, 3-(benzo[d][1,3,2]dioxaborol-2-yl)-1H-indole, 5-bromo-3-(1,3,2-dioxaborolan-2-yl)-1H-indole, 6-methoxy-3-(4,4,5,5-tetramethyl-1,3,2-dioxaborolan-2-yl)-1H-indole, and 5-methoxy-3-(4,4,5,5-tetramethyl-1,3,2-dioxaborolan-2-yl)-1H-indole.

14. A composition according to claim 1, wherein said aromatic system which comprises at least one boronic acid or boronic ester moiety and which is capable of forming upon oxidation a nucleophile or an electrophile is selected from the group consisting of 4-benzoyl-3-hydroxyphenylboronic acid, 4-(3,5-diaminobenzoyl)-3-hydroxyphenylboronic acid, 4-(3,5-dihydroxybenzoyl)-3-hydroxyphenylboronic acid, 4-(2,4-dihydroxybenzoyl)-3-hydroxyphenylboronic acid, 4-(2,4-diaminobenzoyl)-3-hydroxyphenylboronic acid, 4-(2,5-diaminobenzoyl)-3-hydroxyphenylboronic acid, 4-(2,5-dihydroxybenzoyl)-3-hydroxyphenylboronic acid, 4-(2,6-diaminobenzoyl)-3-hydroxyphenylboronic acid, 4-(2,6-dihydroxybenzoyl)-3-hydroxyphenylboronic acid, (4-(1,3,2-dioxaborolan-2-yl)-2-hydroxyphenyl)(phenyl)methanone, (3,5-diaminophenyl)(2-hydroxy-4-(4,4,5,5-tetramethyl-1,3,2-dioxaborolan-2-yl)phenyl)methanone, (4-(1,3,2-dioxaborolan-2-yl)-2-hydroxyphenyl)(3,5-dihydroxyphenyl)methanone, (2-hydroxy-4-(4,4,5,5-tetramethyl-1,3,2-dioxaborolan-2-yl)phenyl)(2,4-dihydroxyphenyl)methanone, (4-(1,3,2-dioxaborol an-2-yl)-2-hydroxyphenyl)(2,4-diaminophenyl)methanone, and (2-hydroxy-4-(5,5-dimethyl-1,3,2-dioxaborinan-2-yl)phenyl)(3,5-dihydroxyphenyl)methanone.

15. A composition according to claim 1, wherein said aromatic system which comprises at least one boronic acid or boronic ester moiety and which is capable of forming upon oxidation a nucleophile or an electrophile is selected from the group consisting of 2-benzoyl-3-hydroxyphenylboronic acid, 2-(3,5-diaminobenzoyl)-3-hydroxyphenylboronic acid, 2-(3,5-dihydroxybenzoyl)-3-hydroxyphenylboronic acid, (2-(1,3,2-dioxaborolan-2-yl)-6-hydroxyphenyl)(phenyl)methanone, (3,5-diaminophenyl)(2-hydroxy-6-(4,4,5,5-tetramethyl-1,3,2-dioxaborolan-2-yl)phenyl)methanone, (2-hydroxy-6-(5,5-dimethyl-1,3,2-dioxaborinan-2-yl)phenyl)(3,5-dihydroxyphenyl)methanone, (2,5-diaminophenyl)(2-hydroxy-6-(4,4,5,5-tetramethyl-1,3,2-dioxaborolan-2-yl)phenyl )methanone, and (2-hydroxy-6-(4,4,5,5-tetramethyl-1,3,2-dioxaborolan-2-yl)phenyl)(2,5-dihydroxyphenyl)methanone.

16. A composition according to claim 1, wherein said aromatic system which comprises at least one boronic acid or boronic ester moiety and which is capable of forming upon oxidation a nucleophile or an electrophile is selected from the group consisting of 2,5,6-triaminopyrimidin-4-yl-4-boronic acid, 6-(1,3,2-dioxaborolan-2-yl)pyrimidine-2,4,5-triamine, 6-(4,4,5,5-tetramethyl-1,3,2-dioxaborolan-2-yl)pyrimidine-2,4,5-triamine, 6-(5,5-dimethyl-1,3,2-dioxaborinan-2-yl)pyrimidine-2,4,5-triamine, and 6-(benzo[d][1,3,2]dioxaborol-2-yl)pyrimidine-2,4,5-triamine.

17. A composition according to claim 1, wherein said auxiliary developer is selected from the group consisting of 2-methyl-benzene-1,4-diamine, benzene-1,4-diamine, 2-thiazole-2-yl-benzene-1,4-diamine, 2-(6-methyl -pyridin-2-yl)-benzene-1,4-diamine, 3'-fluoro-biphenyl-2,5-diamine, 2-propenyl-2-yl-benzene-1,4-diamine, 2-(methoxymethyl)benzene-1,4-diamine, N,N-bis(2-hydroxyethyl)-p-phenylenediamine, 4-amino-phenol, 4-methylamino-phenol, 4-amino-3-methyl-phenol, 1-hydroxy-2,4-diaminobenzene, 2-amino-phenol, 2-amino-5-methyl-phenol, 2-amino-6-methyl-phenol, 1-methyl -1H-pyrazole-4,5-diamine, 1-hydroxyethyl-4,5-diaminopyrazole sulphate, 2-(4,5-diamino-1H-pyrazol-1-yl)ethanol, and mixtures thereof.

18. A composition according to claim 1, wherein said auxiliary coupler is selected from the group consisting of benzene-1,3-diol, 4-chlorobenzene-1,3-diol, 2-methyl-benzene-1,3-diol, benzene-1,3-diamine, 3-amino-phenol, 5-amino-2-methyl-phenol, 1-methyl-2-hydroxy-4-(2'-hydroxyethyl)aminobenzene, 4-methyl-2-phenyl-2,4-dihydro-3H-pyrazol-3-one, 2-aminopyridin-3-ol, 1-phenyl-3-methylpyrazol-5-one, 1-phenyl-3-methyl-5-pyrazolone-2,4-dihydro-5,2-phenyl-3H-pyrazole-3-one, and mixtures thereof.

19. A composition according to claim 1, wherein said aromatic system which comprises at least one boronic acid or boronic ester moiety and which is capable of forming upon oxidation a nucleophile or an electrophile acts as a coupler, and wherein said auxiliary developer is a pyrazole developer selected from the group consisting of 1-methyl-1H-pyrazole-4,5-diamine, 2-(4,5-diamino-1H-pyrazol-1-yl)ethanol, 1-isopropyl-1H-pyrazole-4,5-diamine, 1-(4-methylbenzyl)-1H-pyrazole-4,5-diamine, 1-(benzyl)-1H-pyrazole-4,5-diamine, 1-(4-chlorobenzyl)-1H-pyrazole-4,5-diamine and 1-hydroxyethyl-4,5-diaminopyrazole sulfate.

20. A composition according to claim 1, further comprising at least one additional component selected from the group consisting of direct dyes, oxidizing agents, thickeners, chelants, pH modifiers, buffering agents, and carbonate ion source and radical scavenger systems.

21. A method of oxidatively dyeing hair, said method comprising the steps of:
  (a) mixing a composition according to claim 1 with an oxidizing agent to form a mixture;
  (b) applying said mixture to the hair; and
  (c) rinsing the hair.

22. A hair coloring product in kit form, said kit comprising:
  (a) a first separately packaged container comprising a composition according to claim 1; and
  (b) a second separately packaged container comprising an oxidizing agent.

* * * * *